(12) United States Patent
Sun et al.

(10) Patent No.: US 8,194,247 B2
(45) Date of Patent: Jun. 5, 2012

(54) SHG QUANTIFICATION OF MATRIX-RELATED TISSUE DYNAMIC AND DISEASE

(75) Inventors: Wanxin Sun, Singapore (SG); Henry Yu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 520 days.

(21) Appl. No.: 12/305,349

(22) PCT Filed: Jun. 29, 2007

(86) PCT No.: PCT/SG2007/000194
§ 371 (c)(1),
(2), (4) Date: May 22, 2009

(87) PCT Pub. No.: WO2008/002278
PCT Pub. Date: Jan. 3, 2008

(65) Prior Publication Data
US 2009/0323059 A1    Dec. 31, 2009

Related U.S. Application Data

(60) Provisional application No. 60/817,080, filed on Jun. 29, 2006.

(51) Int. Cl.
*G01J 3/30* (2006.01)
(52) U.S. Cl. .................................................... 356/317
(58) Field of Classification Search .......... 356/317–318, 356/417
See application file for complete search history.

(56) References Cited

U.S. PATENT DOCUMENTS

| 4,796,997 A * | 1/1989 | Svetkoff et al. ............... 356/608 |
| 4,844,617 A * | 7/1989 | Kelderman et al. ........... 356/328 |
| 5,034,613 A | 7/1991 | Denk et al. |

(Continued)

FOREIGN PATENT DOCUMENTS

JP        08-015156        1/1996

(Continued)

OTHER PUBLICATIONS

Cox et al., "3-Dimensional imaging of collagen using second harmonic generation", 2002, Journal of Structural Biology, vol. 141, pp. 53-62.*

(Continued)

*Primary Examiner* — Kara E Geisel
(74) *Attorney, Agent, or Firm* — Knobbe Martens Olson & Bear LLP

(57) ABSTRACT

A microscope for optical imaging of high optical scattering coefficient biological tissue, comprising an optical excitation source for irradiating a scan area of the sample and generating optical emissions, wherein the sample has a first face facing away from the source and a second face facing the source. A two dimensional element for scanning the light over the sample; a focusing element having a numerical aperture NAi to focus the light onto the sample; a first optical condenser to collect light from the first face, the collected light comprising source transmitted light and first optical emission generated in the sample, the condenser having a NA2 larger than NAi; an optical filter to block the transmitted source light; an aperture with a size corresponding to the irradiated area of the sample, the aperture at the conjugate image position of the sample generated by the condenser; and an optical detector collecting light from the first face for detecting the first optical emission from the scan area.

52 Claims, 13 Drawing Sheets

U.S. PATENT DOCUMENTS

| | | | | |
|---|---|---|---|---|
| 5,583,342 | A | * | 12/1996 | Ichie .......................... 250/459.1 |
| 6,169,289 | B1 | * | 1/2001 | White et al. ............... 250/458.1 |
| 2003/0184882 | A1 | | 10/2003 | Engelhardt |
| 2005/0063041 | A1 | | 3/2005 | Sun et al. |
| 2005/0103973 | A1 | | 5/2005 | Abe |
| 2005/0258375 | A1 | * | 11/2005 | Mertz et al. ................ 250/458.1 |
| 2006/0238745 | A1 | | 10/2006 | Hashimoto |
| 2007/0258122 | A1 | * | 11/2007 | Chamgoulov et al. ........ 359/225 |

FOREIGN PATENT DOCUMENTS

| | | |
|---|---|---|
| JP | 10-206742 | 8/1998 |
| JP | 10-253893 | 9/1998 |
| JP | 2001-242383 | 9/2001 |
| JP | 2006-23387 | 1/2006 |
| WO | WO 9746903 | 12/1997 |

OTHER PUBLICATIONS

Prent et al., "Applications of nonlinear microscopy for studying the structure and dynamics in biological systems", 2005, Proceedings of SPIE, vol. 5971, pp. 1-8.*

Yasui, T. et al: "Observation of Collagen Fiber Structure in Dermis Tissue by a Second-harmonic-generation Microscope", SPIE-OSA, vol. 5860, pp. 1-8, 2005.

Banavar, M. et al: "Detection of Collagen by Second Harmonic Microscopy as a Diagnostic Tool for Liver Fibrosis", SPIE, vol. 6089, 2006, 60891B-1-60891B-8.

Cox, G. et al: "Second Harmonic Imaging of Collagen in Mammalian Tissue", SPIE, vol. 4620, pp. 148-156, 2002.

European Supplemental Search Report dated May 31, 2010.

Nikolenko V. et al.; "A two-photon and second-harmonic microscope" Department of Biological Sciences, Columbia University, New York, NY 10027, Methods, vol. 30, No. 1, 2003, pp. 3-15.

Dombeck Daniel A. et al.; "Uniform polarity microtubule assemblies imaged in native brain tissue by second-harmonic generation microscopy", PNAS, Jun. 10, 2003, vol. 100, No. 12, pp. 7081-7086.

Zipfel W.R. et al.; "Nonlinear magic: multiphoton microscopy in the biosciences", Nature Biotechnology, vol. 21, No. 11, Nov. 2003, pp. 1369-1377.

Office Action in Japanese Patent Application No. 2009-518059 dated Feb. 21, 2012.

Office Action in European Patent Application No. 07748739.5 dated Jan. 25, 2012.

Abramowitz, M. et al., "Anatomy of a Microscope: Substage Condensers", Olympus Microscopy Resource Center, pp. 1-4, May 26, 2006.

Cox, G. et al., 3-Dimensional Imaging of Collagen Using Second Harmonic Generation, Journal of Structural Biology, vol. 141, pp. 53-62, Jan. 2003.

* cited by examiner

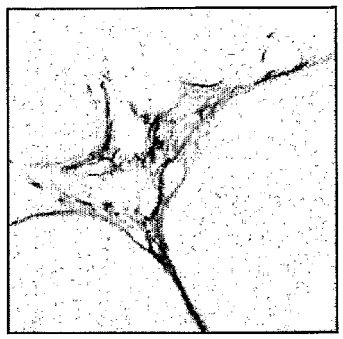 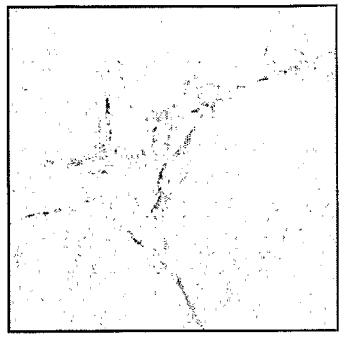 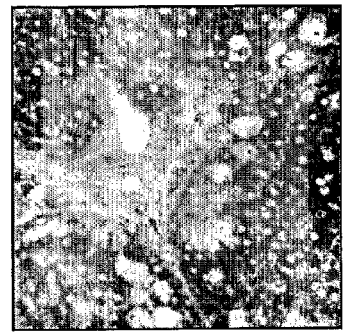
Figure 11A   Figure 11B   Figure 11C
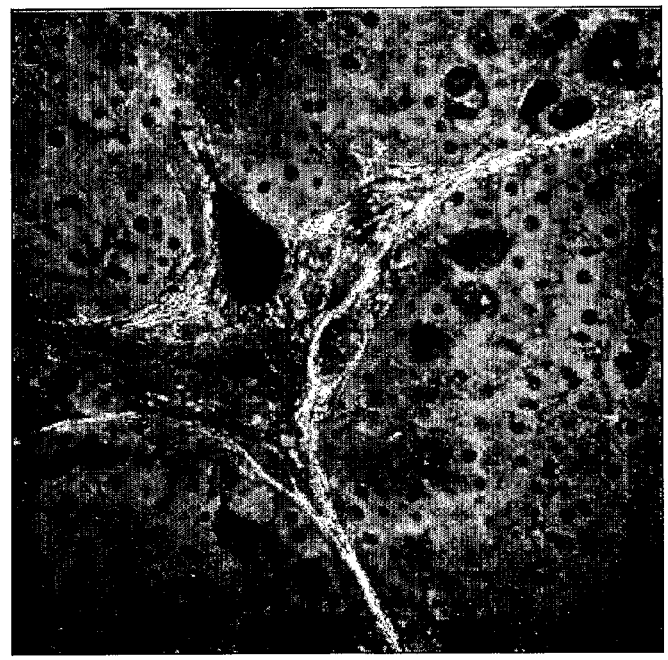
Figure 11D RG Overlay

SHG QUANTIFICATION OF MATRIX-RELATED TISSUE DYNAMIC AND DISEASE

CROSS-REFERENCE TO RELATED APPLICATIONS

This application is the U.S. National Phase under 35 U.S.C. §371 of International Application No. PCT/SG2007/000194, filed Jun. 29, 2007, designating the United States and published in English on Jan. 3, 2008, as WO 2008/002278, which claims priority to United States Provisional Application No. 60/817,080, filed Jun. 29, 2006.

TECHNICAL FIELD

The present invention relates to optical imaging systems and in particular to optical imaging systems for analysis of biological tissue with a high optical scattering coefficient such as liver tissue The invention has been developed primarily for use as an optical imaging apparatus and method for medical analysis of liver tissue and specifically for quantitative characterization of collagen in intact livers tissue structure using nonlinear optical imaging techniques, and will be described hereinafter with reference to this application. However, it will be appreciated that the invention is not limited to this particular field of use.

BACKGROUND

Any discussion of the background art throughout the specification should in no way be considered as an admission that such background art is prior art, nor that such background art is widely known or forms part of the common general knowledge in the field.

Liver fibrosis is a harmful result from a majority of chronic damages to the liver. It is often featured by an abnormal increase of collagen in the extracellular matrix (ECM). Quantitative characterization of collagen in intact tissue structure is therefore essential for understanding and controlling this harmful process.

More generally, liver fibrosis is characterized by increased deposition of ECM, such as fibrillar collagens type I and III, leading to the derangement of liver architecture, portal hypertension, and the development of esophageal varices, edema and ascites. In addition to these changes in morphology, the presence of excess collagen fibers around the hepatocytes impairs their ability to receive enough nutrition, and the accumulation in sinusoids obstructs blood flow, resulting in unhealthy hepatocytes and great decrease in liver function.

Assessing the collagen fibres accurately and dynamically is therefore important for healthcare researchers to monitor the progression, understand the mechanism, and evaluate the therapy strategy.

The classical methods are histological stains (e.g. Masson's trichrome stain, dsmin and vimentin stain etc) and biochemical analysis (e.g. serum laminin analysis). However, traditional histological staining methods limit the assessment to thin tissue slice due to limitations on dye diffusion and the optical penetration of the imaging techniques, and the biochemical analysis loses the spatial distribution information, thereby making it prohibitive to image dynamically in three dimensions (3D).

Furthermore, knowledge of cell morphology information is also important to predict the collagen deposition and distribution during the progression of fibrosis. However, the cell morphology is prone to disintegration during histological staining processes. In addition, for tissue culture work, it is necessary to have enough cell layers in order to keep its structure and functions, and avoid influence on cell behaviour from fluorescence dyes and exogenous proteins for labelling.

All the limitations outlined above make the usual histological staining processes far from ideal. Therefore, it is highly demanded to develop an imaging technique that can accommodate thick tissue slice, in which no staining is required. With the development of mode-lock laser techniques, nonlinear optical microscopy (multi-photon excitation fluorescence and multi-harmonic generation) has been proven to be a promising solution for thick tissue imaging and opens up a realm of thick tissue imaging with a spatial resolution at micrometer scale. The unique advantages of nonlinear optical microscopy include deeper penetration depth, better spatial resolution, intrinsic optical sectioning, and less photobleaching and phototoxicity. Besides these general merits, second harmonic generation (SHG) microscopy, in which two photons are converted into one with double energy and no excited state is involved with a finite lifetime, is sensitive to the alignment, orientation, polarization, and local symmetry of chiral molecules. Therefore SHG can convey rich structural information as well as chemical properties.

Interestingly, some highly-ordered intrinsic structures in cells and tissues, e.g. microtubule, collagen, and myosin, can generate strong SHG signals. By detecting the SHG signals, there is no need to label these structures with exogenous dyes or fluorescent proteins any more, offering a non-invasive methodology to monitor the dynamical changes of tissues in intact state. Due to these unparalleled characteristics, SHG microscopy has attracted extensive attentions in life science and applications have been reported in many varied fields such as in surface property studies, transmembrane potential measurements, and cell imaging to name but a few.

In the tissue imaging realm, SHG images of rat tail tendon were first reported in 1986 and subsequently SHG imaging of other tissues, such as fish scale, skin, the cornea, brain tissue, muscle tissue and tumors have been studied. Among the endogenous proteins, collagen type I was investigated using SHG most thoroughly because of its larger second order susceptibility and well defined structure. To increase the understanding of effects of laser parameters and interpretation of the images obtained, the fundamental principles governing SHG from collagen have also been explored.

However, despite the extensive activity in tissue imaging, nonlinear optical imaging for liver tissue is rarely reported. The main difficulties with nonlinear imaging for liver tissue stem from the fact that liver tissue is a highly light scattering material and there is less fibrillar collagen in normal condition, resulting in shallow optical penetration and weak SHG signals.

Nonlinear optical imaging has been used for analysis of liver tissue by Cox et al. [G. Cox, E. Kable, A. Jones, I. Fraser, F. Manconi, and M. D. Gorrell, 3-*Dimensional imaging of collagen using second harmonic generation*, J. Struct. Biol. 141, 53-62, 2003], however, the reported images were from cirrhotic liver slices (50 μm in thickness), in which much more collagen than fibrosis had been generated.

In order to understand the progression of fibrosis and achieve better prognosis in clinical practices, it is necessary to detect fibrosis from early stage, which requires higher detection sensitivity and better resolution.

SUMMARY

It is an object of the present invention to overcome or ameliorate the disadvantages outlined above, or at least to provide a useful alternative.

According to a first aspect there is provided a microscope assembly for optical imaging of biological tissue, the assembly comprising:

an optical excitation source for irradiating a scan area of a biological tissue sample and generating optical emissions to be emitted from the sample, wherein the sample comprises first and second faces and wherein in use the sample is disposed such that the first face faces away from the excitation source and the second face faces the excitation source;

a two dimensional scanning element for scanning the light from the excitation source over the scan area of the sample; and a focussing element having a numerical aperture $NA_1$ disposed to focus light from the excitation source onto the sample;

a first optical condenser disposed to collect collected light from the first face of the sample, the collected light comprising transmitted light from the excitation source and a first optical emission generated in the sample in response to light from the excitation source, the first optical condenser having a numerical aperture $NA_2$ larger than the numerical aperture of the optical objective $NA_1$;

a first optical filter disposed to block the transmitted light from the excitation source;

an aperture with an aperture size corresponding to the irradiated area of the sample, the aperture being located at the conjugate image position of the sample generated by the first condenser;

a first optical detector disposed to collect collected light from the first face of the sample for detecting the first optical emission from the scan area of the sample.

The microscope may further comprise a collimating lens for collimating the first is optical emission from the sample, the collimating lens located intermediate the aperture and the first detector. The microscope may further comprise a second optical condenser disposed to collect the collimated light and direct it to the first detector. The first optical emission may be a second harmonic optical emission generated in the sample in response to light from the excitation source.

The microscope may further comprise:

an optical spectrometer for selectively detecting the first optical emission from the sample; and a repositionable mirror for selectively directing the first optical emission from the sample either to the spectrometer or to the first detector.

The microscope may further comprise at least one second optical detector disposed to detect a second optical emission from the second face of the sample.

The microscope may further comprise:

at least two second optical detectors disposed to collect collected light from the second face of the sample for detection of a second optical emission from the sample at two different wavelengths, each second detector having a respective optical bandpass filter for selecting a particular optical wavelength band for detection; and at least one optical beam splitter for directing a portion of the second optical emission to each of the at least two second detectors.

The second optical emission from the sample may comprise multi-photon excited fluorescence signal of at least two different wavelengths and the at least two second optical detectors may be configured to detect the multi-photon excited fluorescence signal at each wavelength.

The second optical emission from the sample may be a multi-photon excited fluorescence signal generated in the sample in response to light from the excitation source. The multi-photon excited fluorescence signal may be a two-photon excited fluorescence signal, or it may be a three-, four-, five-, or six-photon excited fluorescence signal.

The second optical emission from the sample may comprise both a multi-photon excited fluorescence signal and a second harmonic generated signal generated in the sample in response to light from the excitation source.

The second optical emission from the sample may comprises both a multi-photon excited fluorescence signal and a second harmonic generated signal generated in the sample in response to light from the excitation source, and one of the two second detectors may be configured for detection of the multi-photon excited fluorescence signal and the other second detector may be configured for detection of the second harmonic generated signal.

The optical excitation source may be a pulsed laser source. The wavelength of the excitation light from the excitation source may be selected such that it falls in a wavelength range where the light scattering of the excitation light and/or the excited SHG signal is relatively weak. The wavelength of the optical excitation source may be in the range of about 880 to 900 nm.

The power of the excitation light from the excitation source that is incident on the sample may be such that it does not cause optical damage to the sample such as, for example, thermal denaturing of the tissue sample. The optical power from the optical excitation source incident on the sample may be in the range of about 5 mW to 300 mW, or alternatively in the range of about 10 to 300, 10 to 250, 10 to, 200, 10 to 150, 10 to 100, 50 to 300, 50 to 250, 50 to 200, 50 to 150, or 50 to 100 mW. The optical power from the optical excitation source incident on the sample may be about 5, 10, 20, 30, 40, 50, 55, 60, 65, 70, 75, 80, 85, 90, 95, 100, 105, 110, 120, 130, 140, 150, 160, 170, 180, 190, 200, 210, 220, 230, 240, 250, 260, 270, 280, 290 or about 300 mW.

According to a second aspect there is provided a method of obtaining an image of a biological tissue sample comprising first and second faces, the method comprising the steps of:

illuminating the biological tissue sample with excitation light from an optical excitation source, the light being scanned over a scan area of the sample, the first face facing away from the excitation source and the second face facing the excitation source, the light being focussed on the sample with focussing element on the second side of the sample, the focussing element having a numerical aperture $NA_1$;

collecting light from the first face of the sample with a first optical condenser, the collected light comprising transmitted light from the excitation source and a first optical emission generated in the sample in response to the excitation light, the first optical condenser having a numerical aperture $NA_2$ larger than the $NA_1$ of the focussing element;

blocking the transmitted light from the excitation source using a first optical filter;

passing the first optical emission through an aperture disposed at the conjugate image position of the sample with respect to the first condenser;

detecting the first optical emission from the scan area of the sample using a first optical detector.

According to a third aspect, there is provided a method of obtaining an image of a biological tissue sample comprising the steps of:

using the microscope of the first aspect, detecting a first optical emission from the sample over a scan area of the sample irradiated by the optical excitation source to generate at least one first image of the first optical emission;

applying a threshold segmentation method to the first image to generate a second image, the second image being a segmented image of the first image;

using the second image as a mask image, multiplying each pixel in the first image with the corresponding pixel of the second image to generate a third image, wherein in the third image the background noise signal in the first image is removed.

The total area characterised by SHG emission and the total intensity of the SHG emission in the third image may be normalised for comparison with other images obtained from different biological samples.

The first optical emission may be a second harmonic optical emission (SHG) generated in the sample in response to light from the excitation source.

According to a fourth aspect, there is provided, a method of determining the severity of fibrosis in a biological tissue sample comprising the steps of:

obtaining an image of a biological tissue sample using the method of the second or third aspects;

determining the normalised intensity of the SHG emission generated in the sample in the image; and relating the SHG intensity to the amount of collagen in the biological tissue, wherein the amount of collagen present in the sample is related to the severity of fibrosis of the biological tissue sample.

According to a sixth aspect, there is provided a method of obtaining an image of a thick biological tissue sample comprising first and second faces, the method comprising the steps of:

irradiating the biological tissue sample with excitation light from an optical excitation source, the light being scanned over a scan area of the sample, the first face facing away from the excitation source and the second face facing the excitation source;

focussing light from the excitation source on to the sample using an focussing element having a numerical aperture $NA_1$;

collecting light from the first face of the sample with a first optical condenser, the second face collected light comprising transmitted light from the excitation source and a first optical emission generated by the sample, the first optical condenser having a numerical aperture $NA_2$ larger than the $NA_1$ of the focussing element;

collecting light from the second face of the sample with the focussing element, the second face collected light comprising a second optical emission from the sample;

detecting the first optical emission from the first face of the sample using a first optical detector; and detecting the second optical emission from the second face of the sample using a second optical detector; and by scanning the excitation source over the scan area, forming first and second images comprising of the biological tissue sample, the first image comprising the first optical emission and the second image comprising the second optical emission generated by the sample.

The first face collected light and the second face collected light may each comprise a second harmonic generated signal generated in the sample in response to light from the excitation source.

The second face collected light may comprises both a multi-photon excited fluorescence signal and a second harmonic generated signal generated in the sample in response to light from the excitation source.

The method may further comprising separating the second harmonic generated signal and the multi-photon excited fluorescence signal in the first face collected light and detecting the second harmonic generated signal with the second detector and detecting the multi-photon excited fluorescence signal with a third optical detector.

The thickness of the sample may be in the range of between about 1 µm and 2000 µm, or alternatively in the range of 1 to 1500, 1 to 1400, 1 to 1300, 1 to 1200, 1 to 1100, 1 to 1000, 1 to 900, 1 to 800, 1 to 700, 1 to 600, 1 to 500, 1 to 400, 1 to 300, 1 to 200, 1 to 100, 1 to 50, 1 to 10 µm.

According to a seventh aspect, there is provided a method of obtaining a three dimensional image of a biological tissue sample comprising the steps of:

repeating the method of the sixth aspect for a plurality of iterations, wherein, for each iteration the light from the excitation source is focused at a different depth in the biological tissue sample, thereby to obtain a corresponding plurality of two-dimensional images of the biological tissue sample, each image corresponding to the optical emission generated in the sample in response to the excitation light at the corresponding focus depth; and combining the plurality of two-dimensional images into a three-dimensional image of the sample.

According to an eighth aspect, there is provided a method of obtaining a three dimensional image of a biological tissue sample comprising the steps of:

repeating the method of the sixth aspect for a plurality of iterations, wherein, for each iteration the light from the excitation source is focused at a different depth in the biological tissue sample, thereby to obtain a corresponding plurality of two-dimensional images of the biological tissue sample, each image corresponding to the optical emission generated in the sample in response to the excitation light at the corresponding focus depth; and for each two dimensional image generating a corresponding plurality of segmented images;

masking the plurality of two-dimensional images with the a corresponding segmented image to remove the background noise in the two-dimensional image, thereby generating a corresponding plurality of noise-corrected images;

combining the plurality of noise-corrected images into a noise corrected three-dimensional image of the sample.

The method of either the seventh or the eighth aspects may further comprise, prior to the combining step, normalising either or both the intensity or the area of each of the plurality of images.

According to a ninth aspect, there is provided use of the microscope of the first aspect for quantification of fibrillar collagen in biological tissue tissue.

According to a tenth aspect, there is provided use of the microscope of the first aspect for monitoring of biological tissue fibrosis. The monitoring of biological tissue fibrosis may be the monitoring of early stage biological tissue fibrosis.

According to a eleventh aspect, there is provided use of the microscope of the first aspect for detection of biological tissue fibrosis. The detection of biological tissue fibrosis may be the detection of early stage biological tissue fibrosis.

According to a twelfth aspect, there is provided use of the microscope of the first aspect for diagnosis of biological tissue fibrosis. The diagnosis of biological tissue fibrosis may be the diagnosis of early stage biological tissue fibrosis.

According to an thirteenth aspect, there is provided use of the microscope of the first aspect for investigating extracellular matrix properties of cancerous tissue.

According to a fourteenth aspect there is provided use of the method of any of the second to eighth aspects for quantification of fibrillar collagen in biological tissue tissue.

According to a fifteenth aspect there is provided use of the method of any of the second to eighth aspects for monitoring of biological tissue fibrosis. The monitoring of biological tissue fibrosis may be the monitoring of early stage biological tissue fibrosis.

According to a sixteenth aspect there is provided use of the method of any of the second to eighth aspects for detection of biological tissue fibrosis. The detection of biological tissue fibrosis may be the detection of early stage biological tissue fibrosis.

According to a seventeenth aspect there is provided use of the method of any of the second to eighth aspects for diagnosis of biological tissue fibrosis. The diagnosis of biological tissue fibrosis may be the diagnosis of early stage biological tissue fibrosis.

According to a eighteenth aspect there is provided use of the method of any of the second to eighth aspects for investigating extracellular matrix properties of cancerous tissue.

In any one or combination of the first to eighteenth aspects, the thickness of the biological tissue samples may be sufficient to allow forward propagating SHG light emissions (in the direction away from the excitation source) excited in the sample by the excitation source to be transmitted through the biological tissue sample or alternatively, backward propagating (that is, in the direction towards the excitation source) SHG light emissions generated in the sample may be detected. Alternatively, both forward propagating and backward propagating SHG light emissions generated in the sample in response to the excitation source may be detected where the thickness of the liver sample permits.

In any one or combination of the first to eighteenth aspects, the biological tissue may be liver tissue.

BRIEF DESCRIPTION OF THE DRAWINGS

Arrangements of the imaging system will now be described, by way of an example only, with reference to the accompanying drawings wherein:

FIG. 5A is an original SHG image obtained directly from the nonlinear optical microscope; FIG. 5B is a segmented binary image obtained through Otsu threshold segmentation; FIG. 5C is the resultant background-screened image; and FIG. 5D is a graph of the pixel grey scale level showing the results of the background screening;

FIG. 7 is a is bright field transmission image of a Manson trichrome stained liver slice, obtained with an ×10 objective and a 5 mega-pixel camera; FIG. 9 is a bright field transmission image of Sirius Red stained liver slice. All of the liver slices are 10 µm in thickness;

FIG. 11D is an overlay of transmission SHG (FIG. 11A), reflection SHG (FIG. 11B) and TPEF (FIG. 11C) images of a 750 µm liver slice, where the TPEF and SHG images have been are generated from hepatocytes and collagen respectively;

DETAILED DESCRIPTION

The obstacles for nonlinear SHG optical imaging of biological tissue having a large optical scattering coefficient, for example liver tissue have surprisingly been significantly overcome with the nonlinear optical imaging system described herein. The optimized second harmonic generation (SHG) microscopy apparatus and method of detection described herein has better resolution and sensitivity than existing imaging apparatus and methods using traditional histological stains, and is able to characterize collagen in 3D in thick tissue slices under physiological conditions without any staining. Together with the collagen quantification algorithm described herein, liver fibrosis progression on rat model has been successfully detected, diagnosed and monitored from very early stage. Furthermore, with the incorporation of SHG imaging with two-photon excited fluorescence (TPEF) for cell morphology observation, SHG microscopy has proven to be an ideal technique for liver fibrosis study. With the presently described system and methods, SHG images of collagen and TPEF images of hepatocytes have been obtained simultaneously from intact thick tissue slices.

To quantify the amount of collagen present in the tissue, an image processing algorithm has also been developed to extract the information pertaining to collagen. The results show that the presently described system is sensitive enough to monitor the collagen change in fibrosis from early stage.

Figure 1:
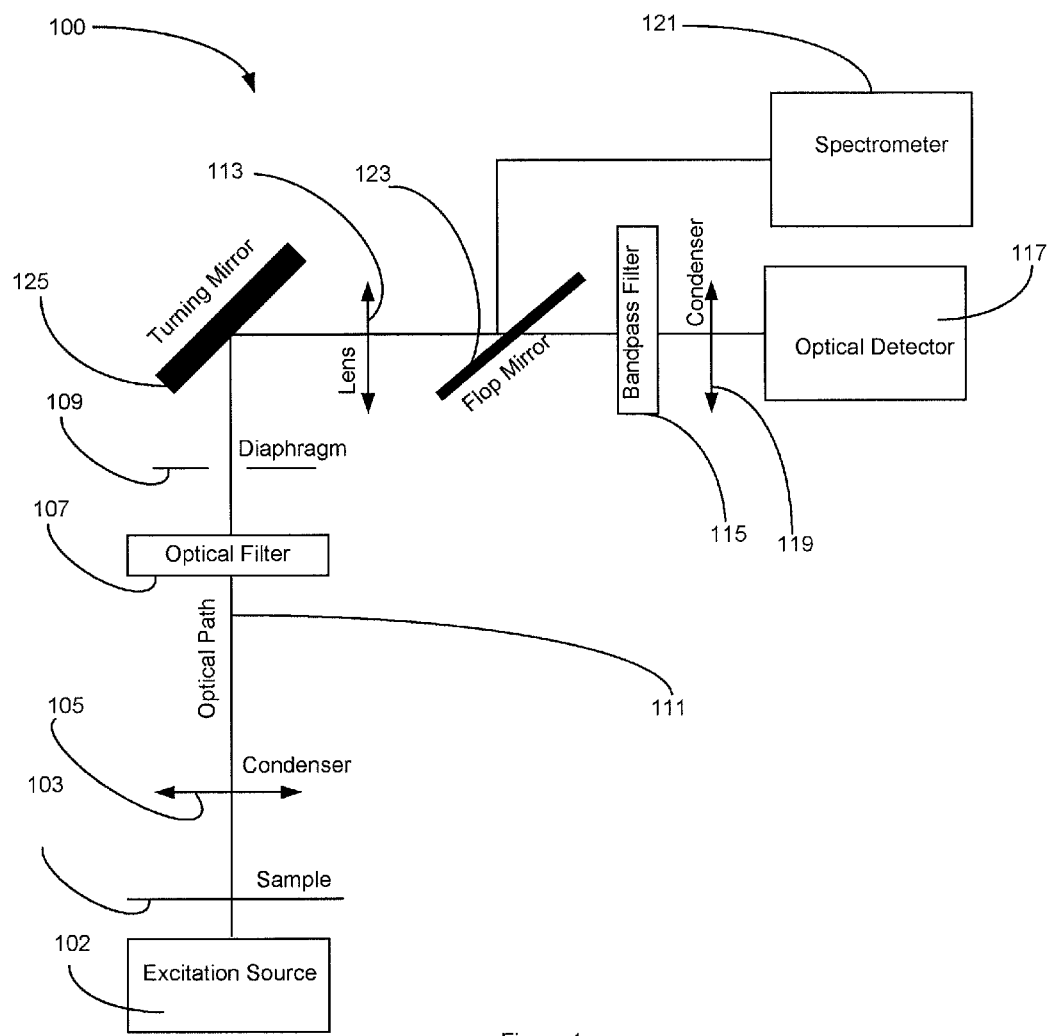
FIG. 1 is a schematic of a nonlinear optical imaging microscope system according to a first aspect.

Referring to the FIG. 1, the collection imaging optics of a first embodiment of the nonlinear optical microscope apparatus 100 is depicted for nonlinear optical imaging of a sample 103. SHG light is excited in the sample 103 in response to excitation light from an excitation source 102, which may be a laser excitation source and may be a pulsed laser excitation source. The power of the excitation light incident on the sample should be such that it does not cause optical damage to the sample such as, for example, thermal denaturing of the tissue sample. The wavelength of the excitation light from the excitation source 102 is selected to be in a range where the light scattering of the excitation light and/or the excited SHG signal is relatively weak.

The SHG light emitted from the sample is then collected by a first optical condenser element 105. The numerical aperture (NA) of the condenser is important for collection efficiency, a NA of between approximately 0.5 to 0.8 is a good compromise between collection efficiency and imaging depth in tissue imaging. Oil immersed condensers which possess a higher NA may also be used, however, these class of condenser elements have a limited focal depth which may causing variation in intensity for different imaging depth.

Any light at the wavelength of the excitation source that is collected by the condenser 105 is removed by at least one optical filter 107. The filter(s) 107 may be short-pass optical filter(s). An adjustable diaphragm 109 (or iris) is located at the conjugate position of the image area. The image conjugation is implemented by positional adjustment of the condenser 105 and/or the diaphragm 109 in 3-space X, Y, an Z dimensions relative to the optical path 111 of the apparatus 100. The adjustable diaphragm 9 is opened to a size corresponding to the scan area of the sample 103. The diaphragm 109 greatly suppresses optical background and noise in the apparatus. After the diaphragm, a lens 113 is used to collimate the optical SHG beam from the sample 103. The optical signal is then filtered by a bandpass filter 115 to isolate the SHG signal from other optical wavelengths and the SHG signal is detected by a sensitive optical detector 117. The detector 117 in the present examples is a photomultiplier tube (PMT) and may be a meshless PMT, however, many other types of optical detector may also be used as will be appreciated by the skilled addressee for example charge coupled device (CCD) detectors which may comprise on-chip CCD detectors and/or CCD detectors with gain, optical detector arrays, photodiodes, among many others.

To concentrate the light on to the detector 117, a second optical condenser 119 is incorporated in the optical path 111 in front of the detector 117. The optical SHG signal from the sample 103 may optionally be switched to a spectrometer 121 by a flop mirror 123 inserted in the optical path 111 for spectral analysis of the SHG signal. A turning mirror 125 may also optionally be used in the apparatus 100 to make the apparatus more compact.

In other examples (not shown) the apparatus may further comprise more than one detector for detecting optical signals from the sample 103, and may have an eyepiece to enable an operator to observe the sample 103. In other examples still, the apparatus 100 may optionally comprise a plurality of detectors. Each of the plurality of detectors may be optimised for detection of a particular optical wavelength. The apparatus may further comprise additional optical turning mirrors and/or optical filters (which may be either band-pass or band-rejection filters) for directing different optical wavelengths to a particular one of the plurality of optical detectors. The apparatus 100 may also comprise a switching device to switch between the detector and the eyepiece, and/or to switch between different types of detector. By mapping point by point in the normal manner, 2D and 3D images may be constructed.

Figure 2:
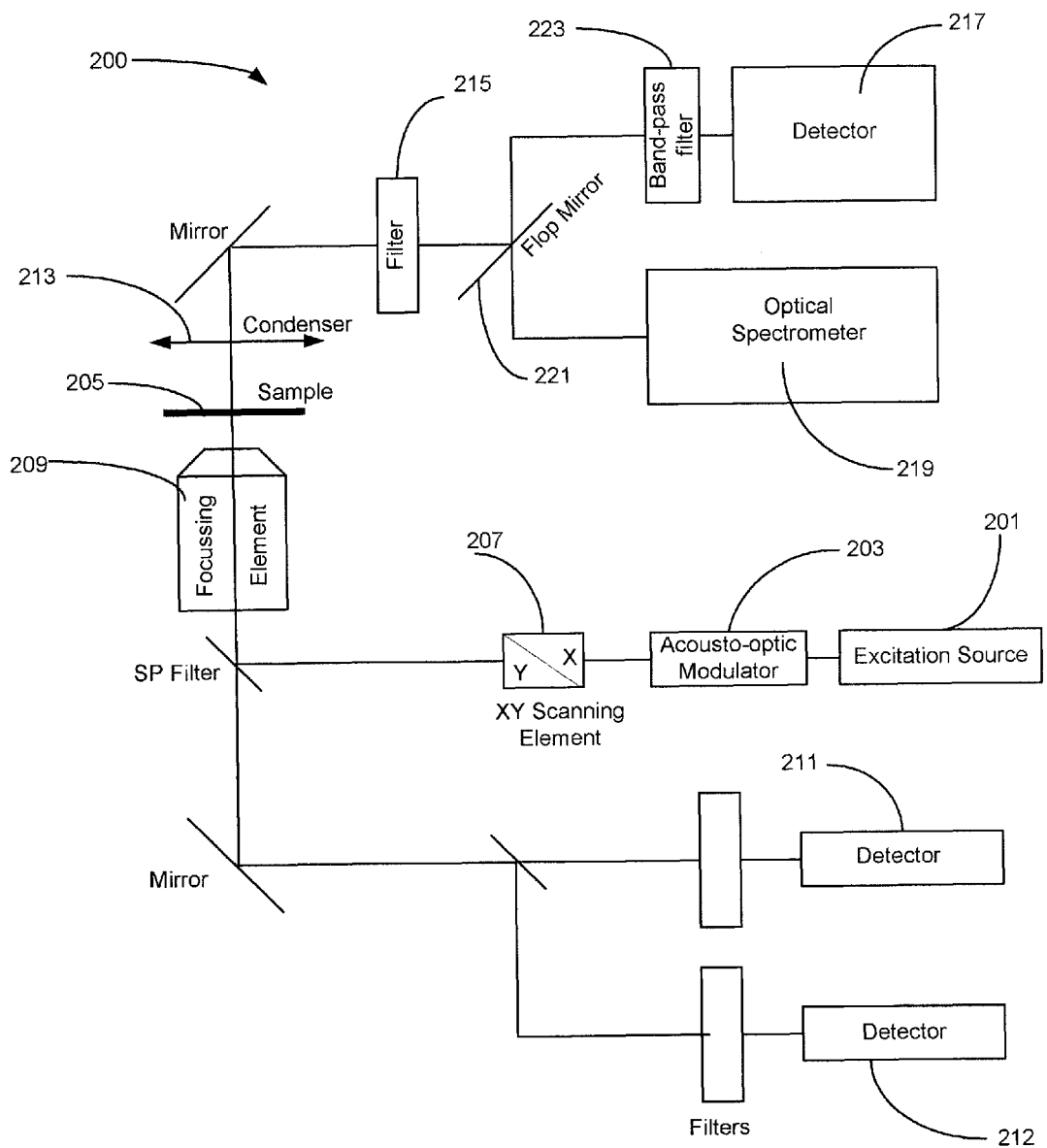
FIG. 2 is a is a schematic of a nonlinear optical imaging microscope system according to a second aspect.

FIG. 2 depicts an example microscope 200 inclusive of the optical excitation source. The microscope 200 has been developed around a Carl Zeiss LSM 510 laser scanning microscope (available from Carl Zeiss MicroImaging, Inc., Thornwood USA). The excitation source 201 is a mode-locked Ti: Sapphire laser (Mai-Tai broadband, Spectra-Physics) with a pulse width of 100 fs and repetition rate of 80 MHz. The laser 201 has a tunable out wavelength of between about 710 to 990 nm. An acousto-optic modulator (AOM) 203 is used to control the laser power reaching the sample 205. After passing through an XY scanning element 207, the laser beam is focused onto the sample 205 by focussing element 209, which in the present examples is depicted as a microscope objective.

In the present example apparatus 200, TPEF is collected in reflection geometry by the objective lens 209 and detected in two channels at different wavelengths by detectors 211 and 212. Detectors 211 and 212 in the present microscope are each PMTs, however, the detectors may 211, 212, and 217 may be one or a combination of other types of optical detectors such as will be appreciated by the skilled addressee for example charge coupled device (CCD) detectors which may comprise on-chip CCD detectors and/or CCD detectors with gain, optical detector arrays, photodiodes, among many others.

The microscope system 200 includes an adjustable iris (not shown) in front of each of the detectors 211 and 212, however, due to the intrinsic optical sectioning capability of the non-linear optical TPEF process, the irises are fully opened.

In contrast with TPEF, the SHG signal is primarily distributed in the same direction as the excitation direction of the laser source (referred to as forward-SHG, which with respect to FIG. 1B is in the upwards direction away from the excitation source 201). The SHG light is collected by condenser 213 and unwanted excess light at the wavelength of the excitation laser is filtered out by a short-pass filter 215. As previously described, the forward-SHG signal may be directed to either a detector 217 (a PMT in the present example) or an optical spectrometer 219 (in the present examples the spectrometer is a model SP2300i spectrometer available from Acton Research) by a flop mirror 221. In front of the detector 217, a band-pass filter 223 is used to remove any TPEF signal and/or stray light from the SHG light from striking detector 217. The band-pass filter may have a transmission bandwidth in the range of 1 to 30 nm, and typically about 10 nm, depending on the bandwidth of the excited SHG light (which in turn will be dependent on the bandwidth of the excitation light as will be appreciated by the skilled addressee).

Alternatively, SHG light may also be generated in the backward propagating direction (referred to as back-SHG) in the direction towards the excitation source. As will be described below, the back-SHG may be detected by either of detectors 211 or 212 (or another similarly located detector) using a suitable combination of mirrors and optical filters as would be appreciated by the skilled addressee. Where the sample provides, both forward-SHG and back-SHG may each be detected, and may be detected simultaneously.

In the present examples, the light is coupled into the entrance slit of the spectrometer 219 by an optical fibre bundle (not shown). After being dispersed by a 1200 g/mm grating, a spectrum is recorded by a thermoelectrically cooled CCD (SPEC-10, available from Princeton Instruments). The PMT detectors 211, 212, and 217 used in the presently described example of the system 200 are Hamamatsu R6357, which is a meshless multi-alkali compact model. By eliminating the mesh from the PMT, high cathode sensitivity (>100 mA/W) and homogenous response of cathode can be achieved, although other suitable types of detectors may be used as would be appreciated by the skilled addressee.

Improvement of Detection Sensitivity

The main obstacle in SHG imaging is its detection sensitivity. To improve the sensitivity, efforts were made to increase the collection efficiency and suppress the background optical signal. Unlike SHG signals from membrane tissue where the emission pattern is confined and a collection numerical aperture (NA) equal to the excitation NA is sufficient to collect all the SHG light, SHG signals from biological tissues with a high optical scattering coefficient, for example liver tissue, is highly scattered and diffused into a wider angle, even in backward direction (towards the excitation source). To improve the collection efficiency, especially for tissue slice samples thicker than 50 μm, an optical condenser having a NA larger than that of the excitation objective was used to collect as many photons as possible. Condensers with NA=0.55 and NA=0.8 were used for 20× magnification (NA=0.5) and 40× magnification (NA=0.75) microscope objectives respectively. The condenser NA may be increased further, however, it is observed that this does not significantly increase the collection efficiency any further. This is because that the scattering of SHG light made it appear that the SHG signal was generated from a much more diffused spot, which can be verified using a Monte Carlo simulation analysis—the large NA limited the focal depth and, as a result, the collection efficiency. Furthermore, the working distance of larger NA condensers is not sufficient to accommodate the incubation chamber, which was used to maintain the temperature, humidity and $CO_2$ concentration of the sample during analysis. These factors therefore make it difficult, if not prohibitive, to use an oil or water immersion condenser during the tissue imaging process.

After the condenser element 205, high throughput optical filters (not shown but analogous to filter(s) 107 of FIG. 1) with optical transmission at the wavelength of the SHG signal of greater than 80% are used to ensure minimal loss of the SHG signal. To suppress the to background, a field diaphragm/iris (not shown, but analogous to iris 109 of FIG. 1) in the conjugate location to the image plane with respect to the condenser element 213 was closed to an aperture size slightly larger than that of the scan area of the sample 205. The iris allowed the signal to entirely pass through while blocking most of the background light. In addition, a black enclosure was used to cover the whole microscope and scanning box to further reduce the background optical signal. To avoid the iris from blocking the SHG signal, the condenser was refocused each time after the sample was changed to ensure that the iris was at the conjugate plane in the imaging system.

Excitation Power

Figure 3A:
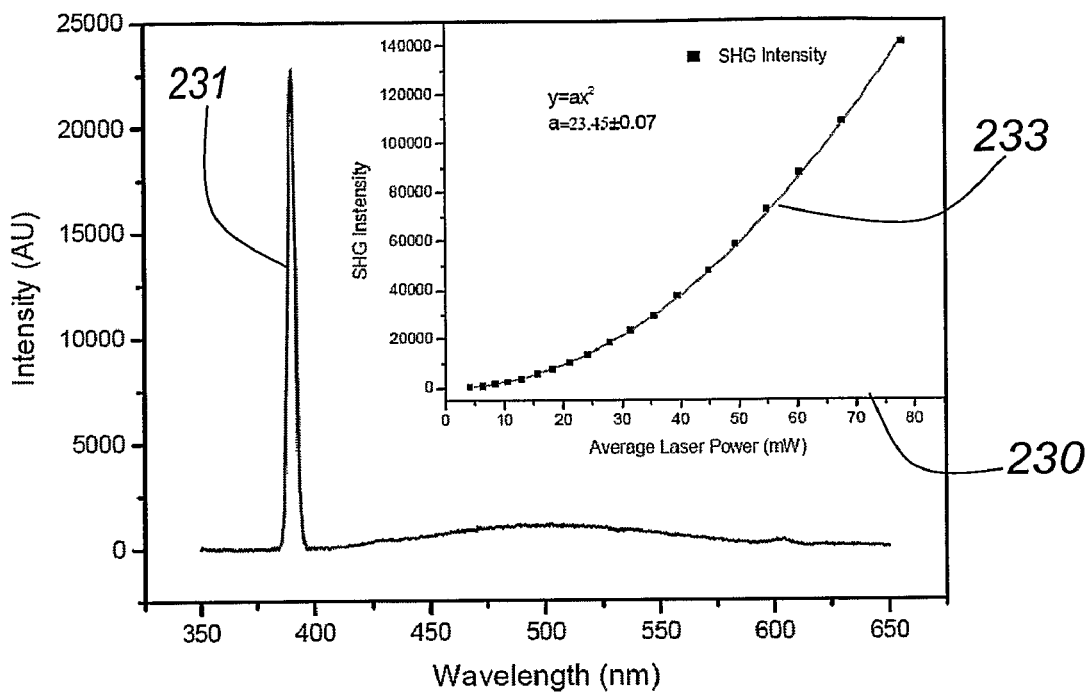
FIG. 3A is a graph of the SHG & TPEF signal output from a liver slice excited with 780 nm, the inset is the dependence of SHG signal intensity on excitation laser power at 900 nm.

As mentioned above, deleterious effects due to photochemical reaction, such as phototoxicity and photobleaching, are negligible in SHG. However, heat generated by laser illumination of the sample can denature the collagen inside the tissue. SHG imaging is a sensitive technique which is able to monitor this denaturing of tissue collagen. Therefore, the power of the excitation light from the excitation source that is incident on the sample is selected such that it does not cause optical damage to the sample such as, for example, thermal denaturing of the tissue sample. To avoid any unfavourable thermal effects from the laser excitation source, the maximum illumination time of each pixel for the resultant image was limited in the present examples to 6.4 μs. Typically, four frames were scanned and averaged by Kalman filter to improve the image quality. To verify the effectiveness of the scan mode, the transmission signal was switched to the spectrometer 219 by switching the flop mirror 221, and SHG spectra are recorded at different excitation powers. The intensity (peak area) is obtained by fitting the SHG peak 231 to a Gaussian profile, as shown in FIG. 3A. The inset 230 of FIG. 3A shows the dependence of the SHG intensity on power incident on the sample 205 from the laser excitation source 201, and is obtained by a bi-directional scan on an small area of the sample viewed at 5× magnification. The parabolic relationship of the graph 233 of the SHG intensity demonstrates that there is no thermal damage of the sample 205 observed even at 80 mW (which was the average power on the sample 205 for the present examples). Under normal one-directional scan, the sample can sustain even higher incident powers, potentially up to 300 mW of incident power or greater.

Excitation Wavelength

Figure 3B:
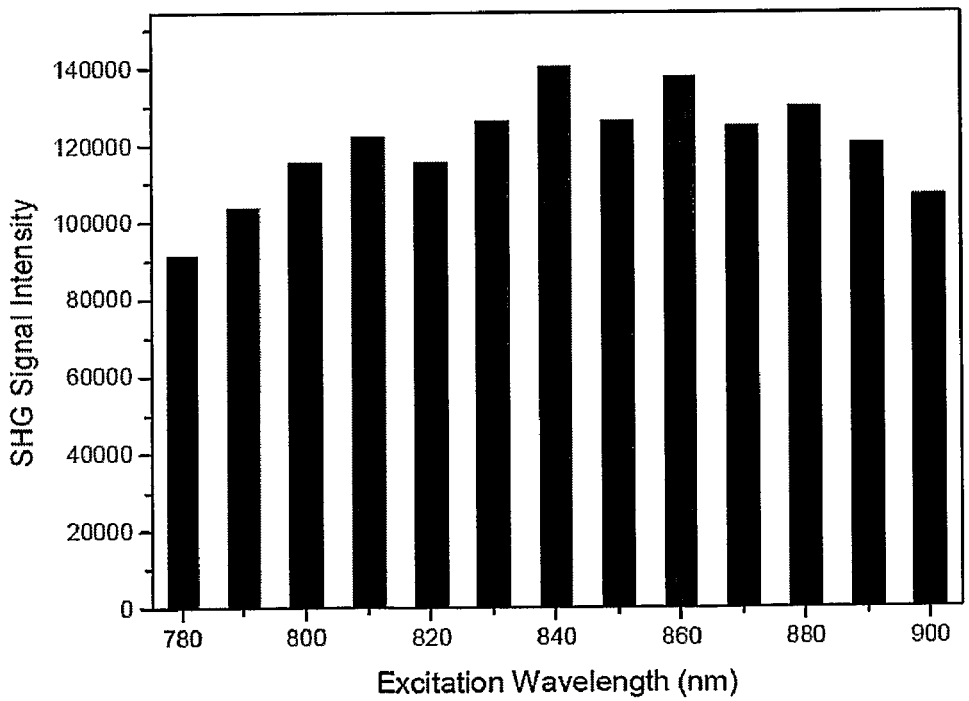
FIG. 3B is a graph of the dependence of the SHG intensity on the wavelength of the excitation source with constant incident excitation power.

Although the SHG imaging process is a non-absorption process, the SHG signal can be enhanced by resonance, wherein the wavelength of the SHG signal falls into a two-photon absorption band of the sample. Depending on the specific properties of the molecule in the sample, resonance can produce an enhancement of an order of magnitude or more. With the aim to improve the detection sensitivity, both SHG and TPEF are recorded for different excitation wavelengths (i.e. by tuning the wavelength of the laser source). Since the laser power of the Ti:sapphire laser 201 used in the present microscope varies with wavelength, the AOM 203 was is tuned to make sure the excitation power on sample was the same for each wavelength. The excitation power was verified with a power meter (Melles Griot power meter model no. 13 PEM001). As can be seen in FIG. 3B, the intensity (peak area) of the SHG signal does not change significantly with excitation wavelengths. For thin tissue slices of the order of 10 μm, different wavelengths produce similar SHG intensity for collagen in liver tissue. However, light scattering limits the penetration depth and deteriorates spatial resolution. The wavelength of the excitation light from the excitation source is selected to be in a range where the light scattering of the excitation light and/or the excited SHG signal is relatively weak. Excitation light having a wavelength in the range of about 880-900 m is used for imaging of liver tissue in the present example since it was found that the light scattering is relatively weak at these wavelengths. The choice of this wavelength range in the present discussion is of course limited only by the tuning range of the available laser source. Other suitable wavelengths either longer than 900 or shorter than 880 nm may also be utilised with an appropriate laser source such as a solid state laser source, a diode laser source, dye laser source or other suitable source. The laser may also not necessarily be a tunable laser source and instead be a laser with a fixed output wavelength (having a finite emission bandwidth as appreciated by those skilled in the art) may also be used once a suitable wavelength is determined which gives efficient SHG generation in the same considering the above factors.

Quantification Algorithm

This section presents a quantification algorithm for the determination of fibrillar elements in a biological sample, an example of which is fibrillar collagen in liver tissue and the present discussion will particularly describe this example, however it will be appreciated that the technique is applicable in other examples.

Figure 4A:
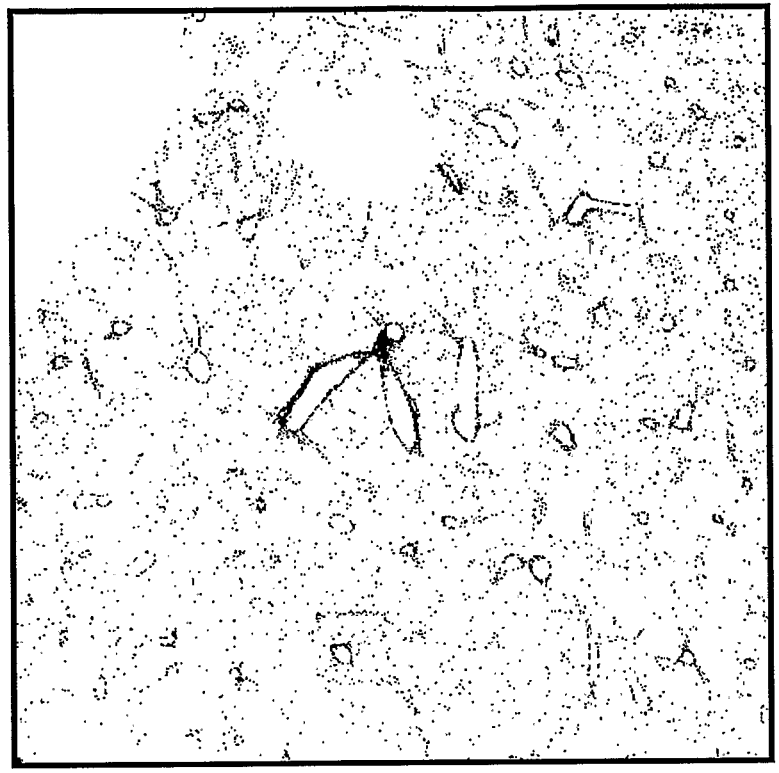
FIGS. 4A and 4B respectively are SHG images (negative image) of normal (4A) and fibrotic (4B) liver slices obtained through tile scan.
Figure 4B:
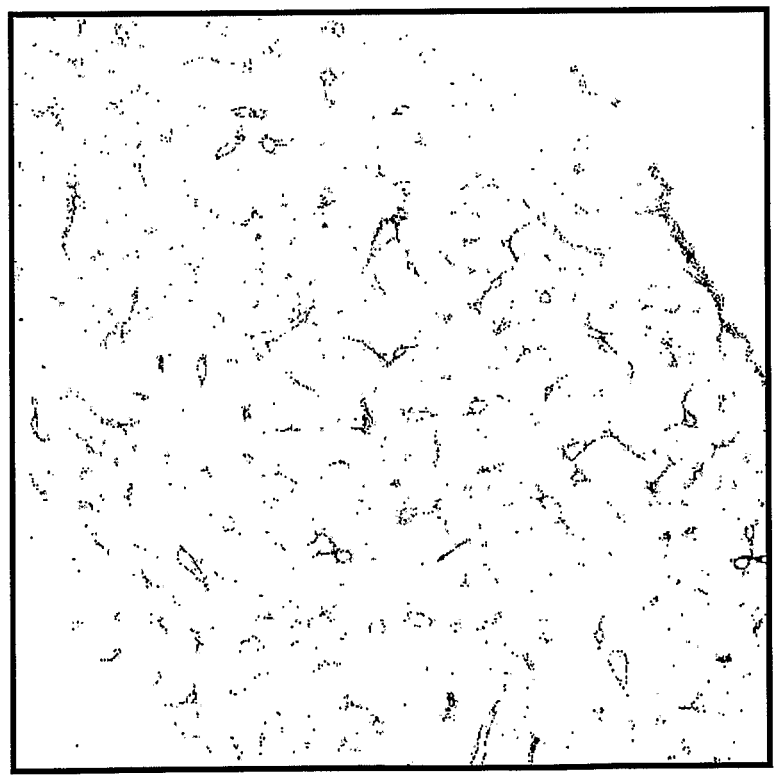

The amount of collagen in liver tissue is a direct measurement of the severity of fibrosis. FIGS. 4A and 4B are images showing the SHG optical signal from a normal and a fibrotic liver slice respectively (these figures are negative images for ease of reproduction). The obvious difference in collagen between the normal and fibrotic livers validates the effectiveness of SHG. Besides the qualitative information obtained from the SHG images, quantitative characterization of the images enable a more accurate description of the progression of fibrosis to be made, which is critical to understand the underlying mechanism and to evaluate the effectiveness of treatments.

Like other imaging techniques, noise and background in SHG images are unavoidable, and the background level may vary from experiment to experiment. Therefore, segmentation was first applied to the original images to separate collagen from the background. For simplicity in implementation, threshold segmentation was adopted as would be appreciated and understood by the skilled addressee in medical imaging analysis. The Otsu method [see N. Otsu, *A threshold selection method from grey level histograms*, IEEE Trans. System, Man and Cybernetics. 9, 62-66, 1979] was used to optimize the threshold for each image as described below.

For each threshold t, an image is split into two groups (object and background) and the weighted sum of intragroup variances, $\sigma_w^2$, is calculated as follow. The sum $\sigma_w^2$ is defined by:

$$\sigma_w^2(t) = q_1(t)\sigma_1^2(t) + q_2(t)\sigma_2^2(t) \quad (1)$$

where $$q_1(t) = \sum_{i=0}^{t-1} p(i), q_2(t) = \sum_{i=t}^{N} p(i),$$

p(i) is the probability of the histogram at grey scale i, and N is total number of grey scale levels in the image. $\sigma_1^2(t)$ is the variance of the pixels in the first cluster (<t, where t is the background), and $\sigma_2^2(t)$ is the variance of the pixels in the second cluster ($\geq$t, which is object). Then $\sigma_w^2$ is computed for all possible values of t, and the t value producing the smallest $\sigma_w^2$ is the optimal threshold T. In brief, after the all the grey scale levels in the image are scanned, the value that minimizes the total weighted intragroup variance is the optimal threshold. The algorithm has been implemented for the present system using Matlab (Matlab R14, available from The Math Works, Inc, Natick). Since the threshold segmentation method processes each pixel independently, grainy noise will affect segmentation. To remove the isolated pixel noise and join separated portions of features in the binary images generated by the segmentation, erosion and dilation operations were applied to improve the accuracy of quantification.

Figure 5A:
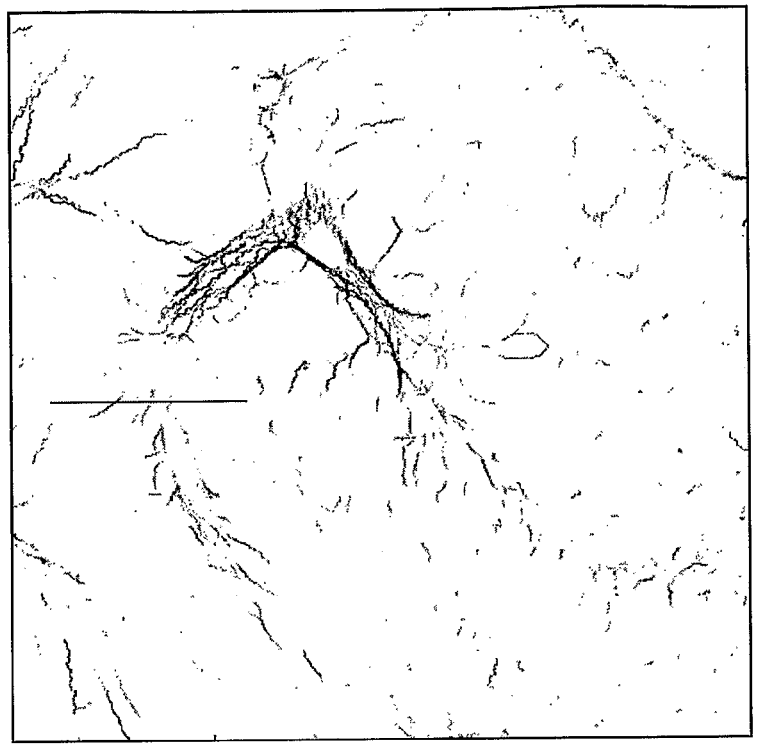
FIGS. 5A to 5D show an example illustration of the image quantification procedure.
Figure 5B:
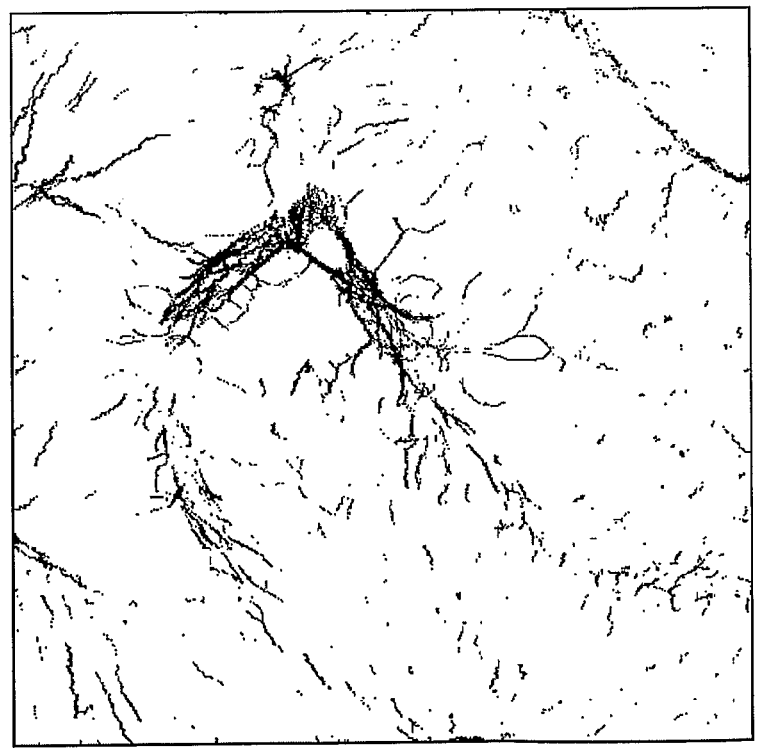

As an example, an original SHG image and a segmented image are shown in FIGS. 5A and 5B respectively. From the segmented image, FIG. 5B, the total area of collagen is calculated.

Figure 5C:
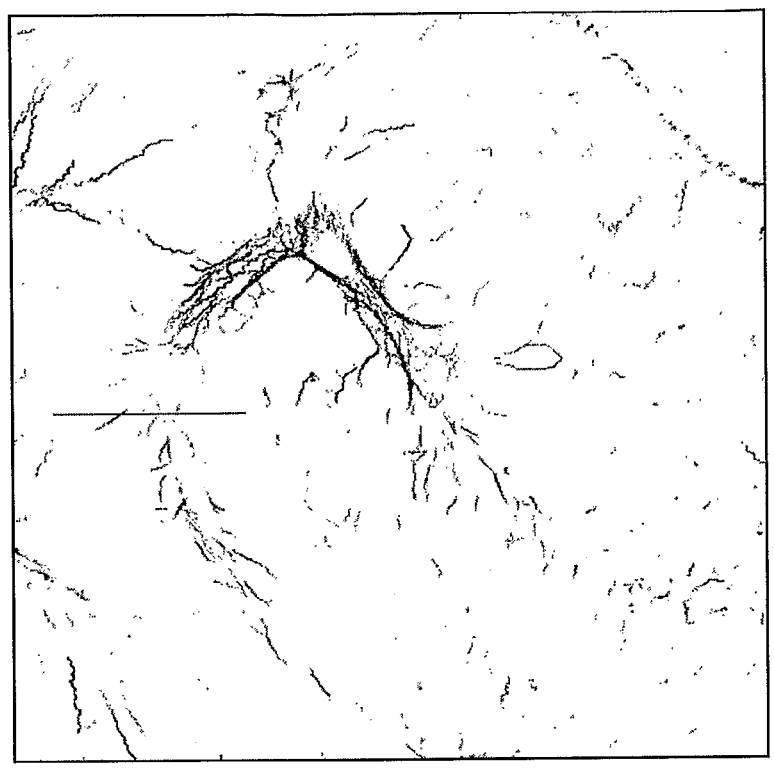
Figure 5D:
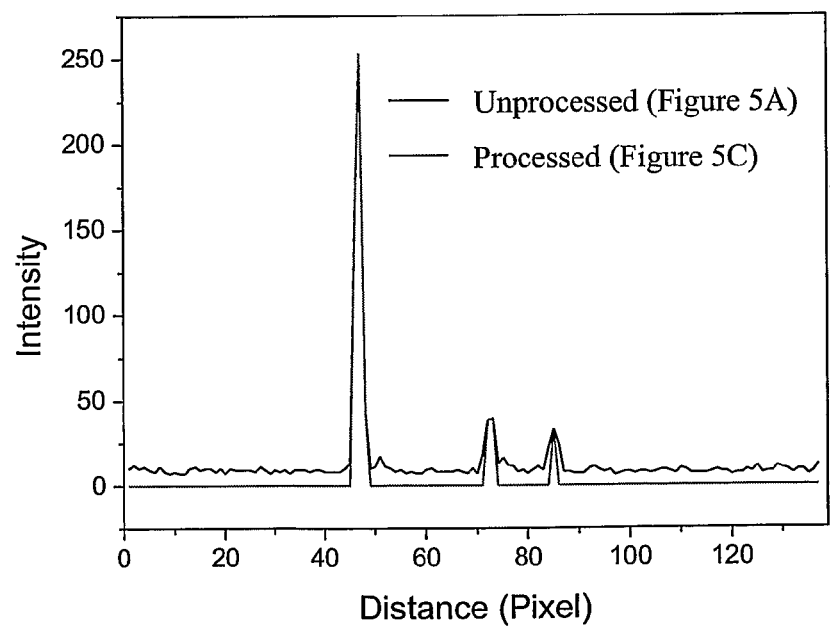

Another parameter used to quantify the collagen is total SHG intensity. If the summation is done over the whole image, the background level and noise significantly affects the resulting analysis. To rule out the deleterious effect of the background noise, the segmented image is used as a mask to screen out the background in the original image. This is implemented by multiplying the original image (i.e. FIG. 5A) with the mask image (i.e. the segmented imaged of FIG. 5B) pixel by pixel. Only the intensity of the collagen signal for each pixel is counted. The total area and total intensity are then normalized to the whole area of the image to make the quantities comparable for different experiments. FIG. 5C is the result of the background-screened image using this method and the resulting reduction in background can be seen in FIG. 5D which is a graph of the pixel grey scale level (i.e. intensity of the collagen signal for each pixel) along lines 251 and 253 (respectively lines 252 and 254 in FIG. 5D) of FIGS. 5A and 5C respectively. (Note that FIGS. 5A, 5B and 5C are negative images for ease of reproduction.)

Figure 6:
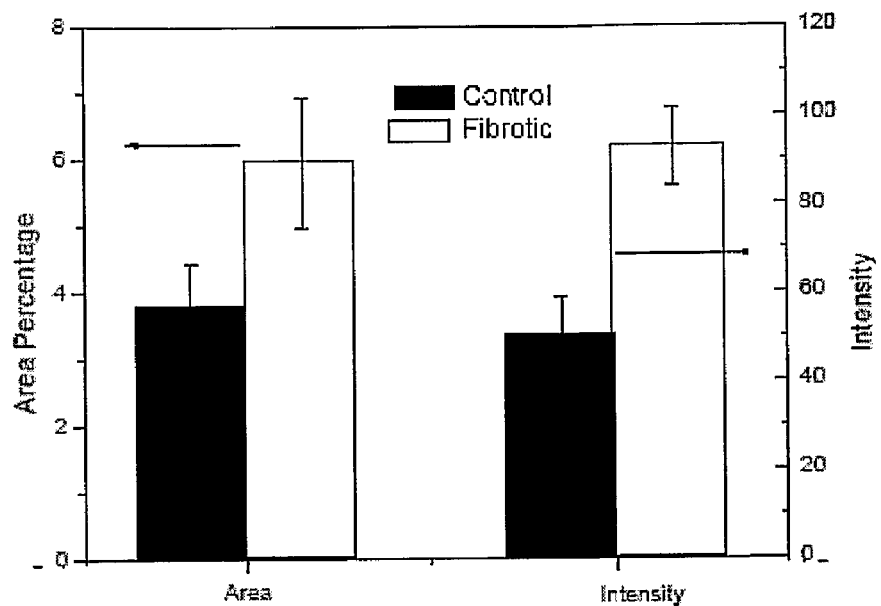
FIG. 6 is a graph showing the area percentage and average intensity of collagen in normal and fibrotic livers.

FIG. 6 shows the area percentage (normalized area) and average intensity (normalized intensity) of collagen for normal and fibrotic livers. It is noticed that the difference in average intensity is more pronounced. This can be explained by the fibrosis process, during which more collagen fibres are generated. Some of collagen fibres are dispersed in tissue as tiny fibres whereas others form thick bundles, as demonstrated by the SHG images. For thick bundles, SHG intensity increases at pixel level, as well as the total number of bright pixels (the area) Besides the thickness of bundles, the collagen fibrils consistently grow thicker, resulting in increased SHG intensity even without increase in area. Therefore, the change in total intensity represents the fibrosis progression more closely than the total area.

EXAMPLES

SHG and TPEF imaging of liver tissues are presented in the following examples.

Sample Preparation—Liver Fibrosis Induction

Male SPF Wistar rats, with initial body weight of 90 to 100 g, were housed with free access to lab chow and water in a 12:12-hour light/dark schedule. Carbon tetrachloride ($CCl_4$) was injected intraperitoneally (100 µL, diluted 1:1 in vegetable oil) 3 times a week to induce liver damage. A control group was injected with vegetable oil only with the same dosage. Liver tissue was harvested from both groups at different time points, with an interval of 2 days after the last injection. Before each harvest, the animals were fasted over night and deeply anesthetized with sodium pentobarbital (40 mg/kg body wt). After that, the animals were sacrificed. All procedures performed on rats were approved by the Institutional Animal Care and Use Committee and within the guidelines for humane care of laboratory animals.

Tissue slices thinner than 50 µm were sectioned by cryosectioning (using a Leica CM 3050S cryostat device available from) at −20° C. Slices thicker than 50 µm were sectioned by vibratome (3000 plus available form Ted Pella, Inc Redding, Calif. USA), where the bath and medium were cooled to 4° C. by a Peltier device to maintain the structure.

Example 1

Comparison Among SHG, Masson's Trichrome, and Sirius Red Staining

Figure 7:
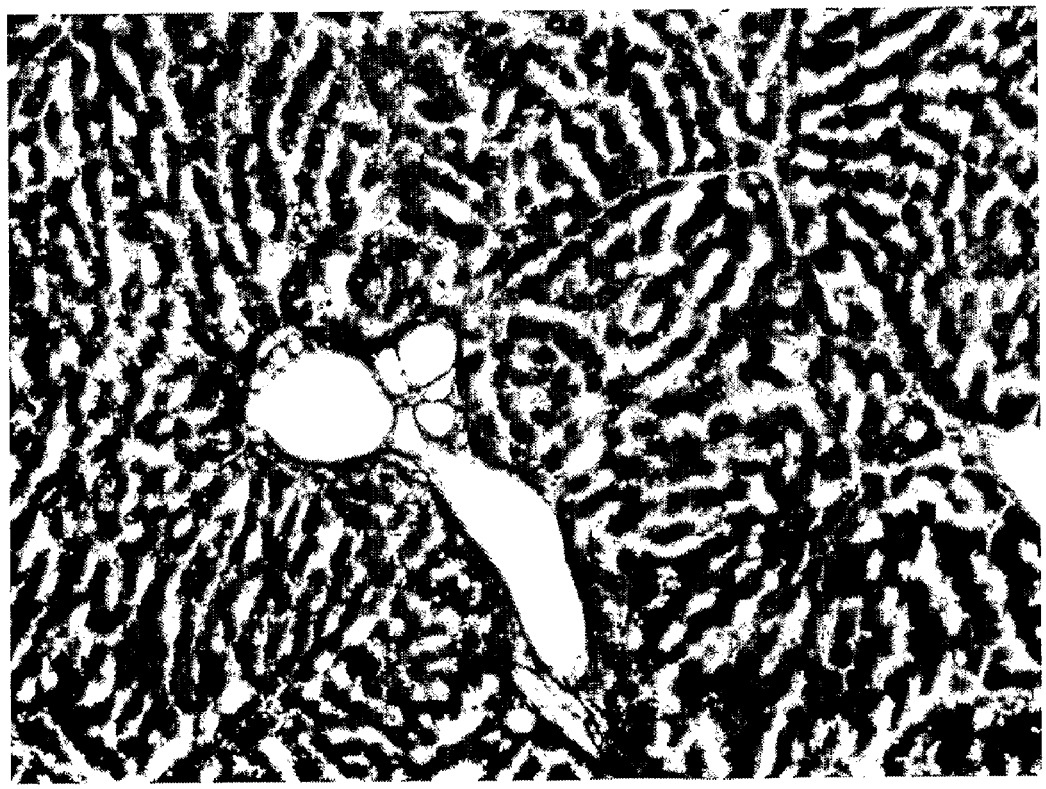
FIGS. 7, 8 and 9 show comparative images respectively for SHG imaging, Manson trichrome stain, and Sirius Red stain for a liver slice 10 µm in thickness.
Figure 8A:
FIG. 8C is the overlay of SHG (FIG. 8A) and TPEF (FIG. 8B) images from a unstained liver slice, obtained with an ×10 objective (NA=0.5) and 900 nm excitation.
Figure 8B:
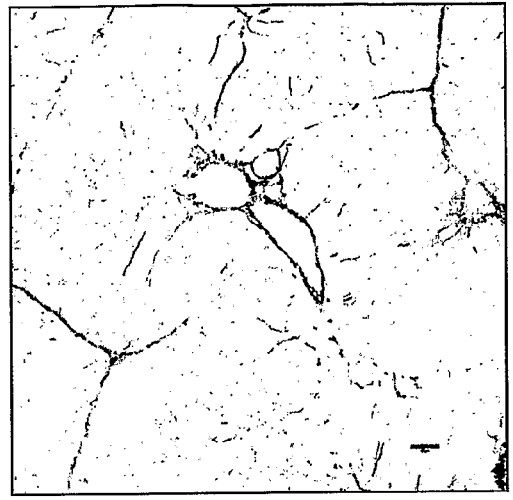
Figure 8C:
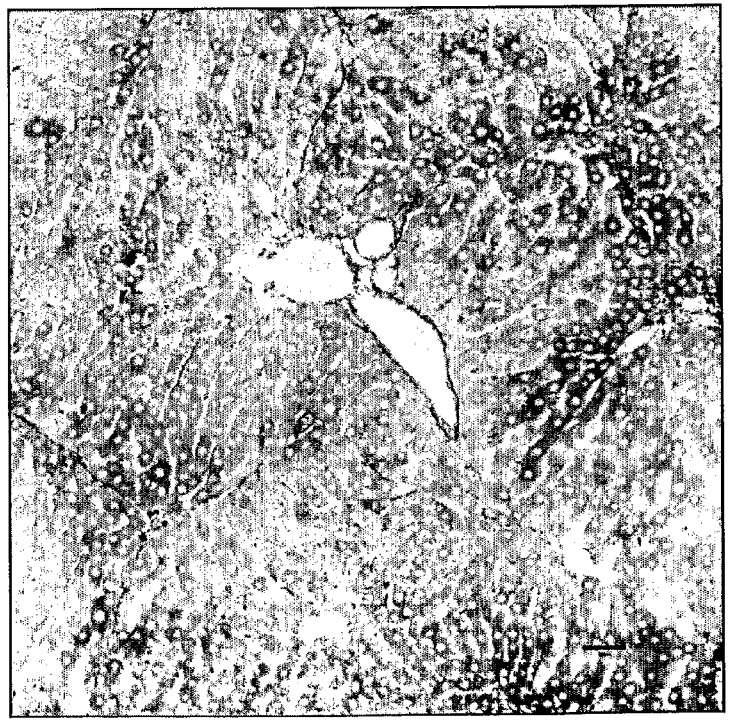

To compare the sensitive and spatial resolution of SHG microscopy with traditional histological stains, two slices (10 µm in thickness) were successively cryosectioned from a piece of liver. One slice was stained with Masson's trichrome method, and the other one was mounted on a microscope slide without specific preparation for SHG and TPEF microscopy. FIG. 7 (positive image) shows the bright field transmission image of the stained slice recorded by a 5M-pixel camera (MicroPublisher 5.0 RTV, available from QImaging). The overlay of SHG (FIG. 8A) and TPEF (FIG. 8B) microscopy is shown in FIG. 8C (the images in FIGS. 8A, 8B and 8C are negative images for ease of reproduction). Comparing the FIGS. 7 and 8C, both methods produced similar results for thick collagen bundles. However, thin collagen fibres between hepatocytes are clearly discerned in the SHG image (FIG. 8A) while the trichrome image (FIG. 8B) fails to produce any contrast. This is attributed to the difference in contrast mechanism. In trichrome staining, the dye on collagen absorbs red light and makes it appear blue. If a fibre is too thin to absorb enough red light to show blue colour, it disappears in the transmission image. In SHG imaging, tiny fibres generate SHG signal when excited with femtosecond pulses. Although the SHG signal generated by the thin fibres is weaker than the signal generated by the thick fibres, it is still picked up by the sensitive detection apparatus described above, thus forming clean contrast with dark background.

Another commonly used method to quantify collagen is Sirius red staining. To make a comparison with SHG, a 10 µm liver slice was stained with Sirius red and a bright-field transmission image (shown in FIG. 9—positive image) was recorded with the same CCD camera mentioned above. Similar to the Masson's trichrome image of FIG. 8B, the information of the tiny fibres was lost. Fortunately, Sirius red emits fluorescence when excited with 543 nm laser and has been used in confocal fluorescence microscopy. To confirm the tiny fibers are collagen, fluorescence and SHG were recorded to obtain similar images to those of FIGS. 8A and 8B. The co-localization of the two signals shows that the tiny fibres appeared in the SHG images are collagen. However, the fluorescence of Sirius red overlaps the autofluorescence of liver, making it difficult to use Sirius red stain for collagen quantification. On the contrary, SHG produces a clean background.

Figure 9:
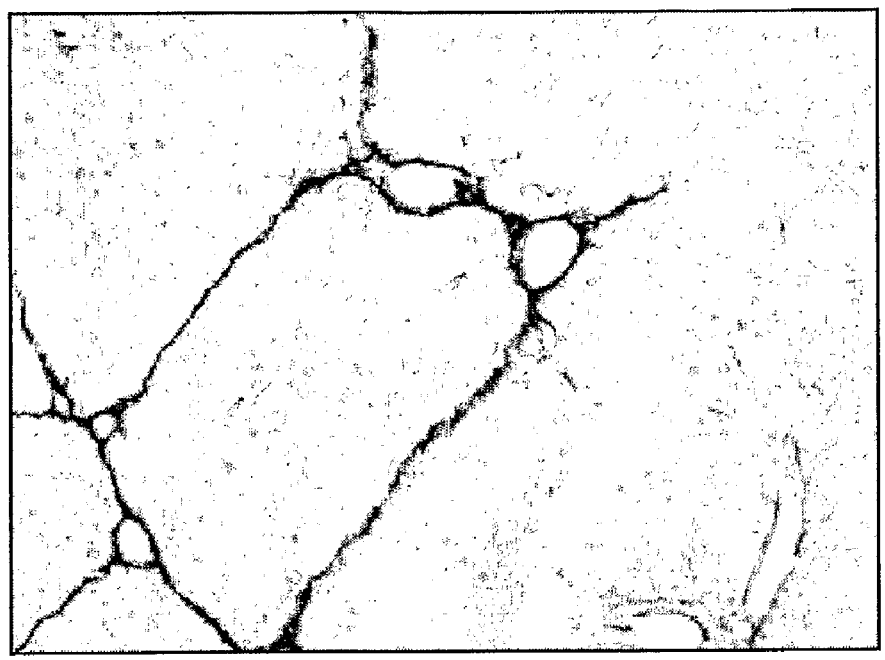

Physicians normally evaluate fibrosis and make prediction on progression using cell morphology as well as collagen quantity. Besides sensitivity and resolution, preservation of cell morphology is another advantage of SHG. The morphology of liver tissue slice was well preserved in the SHG microscopy since there was no sample preparation required. In histological staining, the slices were subject to many processes, e.g. hydration, dehydration, rinsing, and chemicals. As a result, the morphology changed and space in sinusoids increased, as shown in FIGS. 7 and 9.

Example 2

Detection, Diagnosis and Monitoring of Early Stage Liver Fibrosis

As seen in the results of Example 1, through optimizing the optical configuration and detection system, SHG imaging demonstrates better sensitivity and spatial resolution than histological stains. In this example, SHG imaging was used to monitor liver fibrosis progression, however it will be appreciated that the examples described herein may also be used for diagnosis of liver fibrosis in a liver sample and/or detection of fibrosis per se in a liver without requiring known imaging methods requiring staining of the sample. Because no staining is required and deep penetration is achieved by infrared excitation, 50 µm liver slices were used in the present example.

The output from a laser excitation source was focused to the middle of the slices to record the intact structure. To obtain statistically significant data, 6 slices were scanned for each sample. Depending on the size, 2~3 images (3.68×3.68 mm$^2$) were scanned for each slice. The large images were constructed by tile scan controlled by computer, where a 0.46× 0.46 mm$^2$ image was formed by scanning laser beam as in normal confocal microscopy. Upon the completion of each small image, the sample was translationally shifted one image size by a motorized stage. An 8×8 image matrix was stitched to form a large image. After acquisition, the images were processed by algorithm mentioned above.

Figure 10:
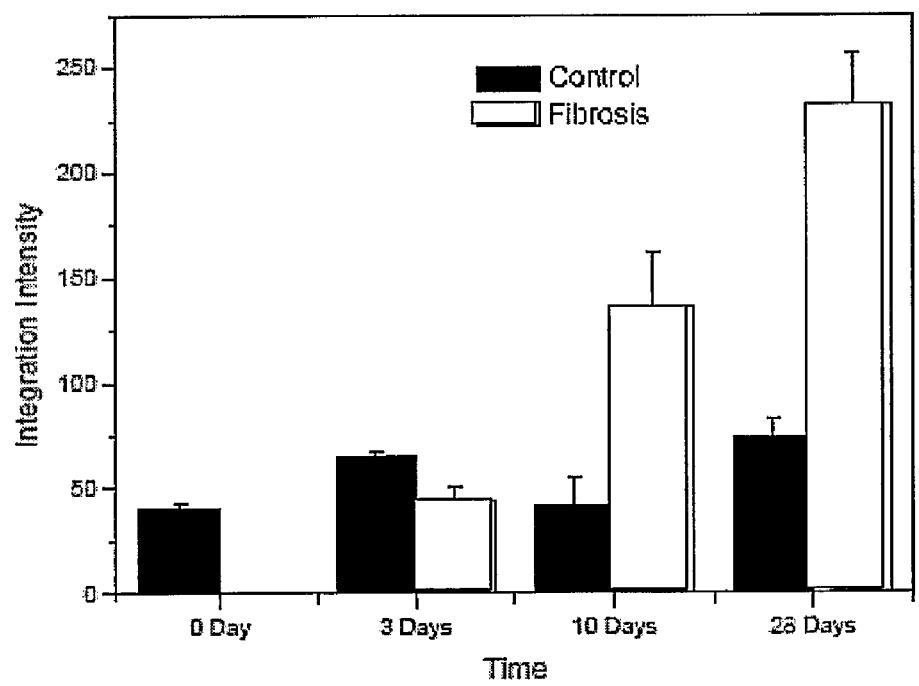
FIG. 10 is a graph of the average intensity of collagen from control group and fibrotic group at different time points.

FIG. 10 shows the average intensity of collagen from livers harvested at different times. The control group does not show significant change in collagen as expected. However, the fibrotic group shows dramatic increase from day 10. The average collagen intensity of control group is 55. For the fibrotic group, the average intensity increases to 136 and 231 at day 10 and day 28 respectively. In spite of the fact that no experiments were performed between day 3 and day 10, it is reasonable to expect from the results shown in FIG. 10 that the SHG signal analysis technique is capable of detecting the collagen change before day 10. This result demonstrates that the SHG system is sensitive enough to detect fibrosis from the early stage.

Example 3

Imaging of Thick Tissue Slices and Whole Liver Lobe

Besides better resolution and sensitivity, another aim of the present system an apparatus is to increase the penetration depth. To verify whether the SHG system can be used to image thick liver tissue, a 750 µm liver slice sample was imaged. The sample was put into a glass bottom dish and immersed in Phosphate Buffered Saline (PBS). A 22×22 mm$^2$ cover slip was then placed on the top to prevent it from floating. Interestingly and unexpectedly, SHG signals in both transmission and reflection were observed as shown in FIGS. 11A and 11B respectively (negative images). FIG. 11C (positive image) shows the TPEF from the same sample and FIG. 11D is a positive image overlay of FIGS. 11A to 11C. The TPEF and SHG are generated from hepatocytes and collagen respectively For the size of the collagen fibre, backward SHG is about one order of magnitude weaker than the forward, resulting in the dominance of the forward SHG for thin slices. For thick slices, the observed SHG in reflection geometry is mainly contributed by scattered forward SHG. During the propagation through the sample, the forward SHG signal is multi-scattered as the light scattering coefficient of liver at SHG wavelength is large (about 200 cm$^{-1}$) even though the scattering coefficient at the fundamental laser excitation wavelength (~900 nm) is small.

Figure 12:
FIG. 12 is a projection of a 300 µm thick Z-stack obtained from a whole liver lobe in reflection configuration.

This therefore provides the opportunity to image whole liver organs using SHG signals with a reflection optical collection geometry. Similar to the imaging of the thick slice, a liver lobe was put into a glass bottom dish, which contained enough PBS to prevent it from drying out. A plurality of images in the z-direction (i.e. in the direction of forward propagation of the laser excitation beam) though the liver lobe and projected into a 3D view, as shown in FIG. 12 (negative image). Tiny fibres can be clearly discerned in the image.

It should be noted that the spatial resolution of nonlinear optical microscopy is governed by the focal volume of the laser beam. Light scattering diffuses the SHG and TPEF signals and weakens them to some extent. Even so, however, the resolution is not affected, unlike chemiluminescence or single photon fluorescence images of tissues recorded by a high sensitive camera or scanning probe microscopy.

Example 4

Quantitative Study of Tumor ECM Dynamics by SHG Imaging

Extracellular matrix (ECM) provides mechanical support and a variety of signalling molecules for cancer cells. Cancerous ECM can also initiate the oncogenic transition of normal cells. Understanding how ECM participates in the abnormal growth is fundamental to understanding cancer and may suggest therapeutic approaches to regulate the abnormal growth.

Figure 13A:
FIG. 13C is an overlay of TPEF (FIG. 13A) and SHG (FIG. 13B) in cancerous tissue.
Figure 13B:
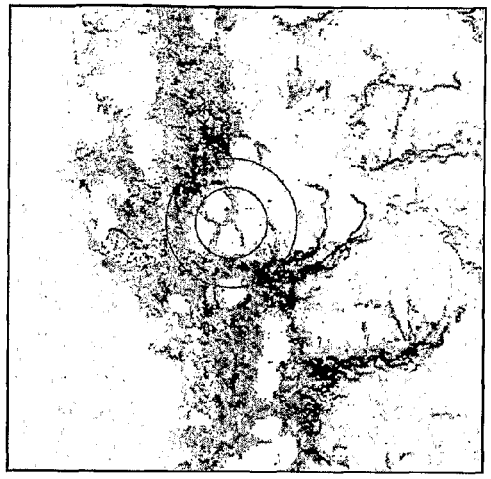

In this example, SHG microscopy was used to investigate ECM in cancerous tissue sensitively and quantitatively. The tumor model was developed by subcutaneous injection of human breast cancer cells (MCF-7 transfected with red fluorescence protein for easy monitoring of tumor growth in vivo) into severe combined immune deficiency (SCID) mice. Two photon excited fluorescence (FIG. 13A) and SHG (FIG. 13B) indicate the cancer cells and ECM respectively (negative images). FIG. 12C is a negative image of the overlay of both the TPEF and SHG signals. Tiny fibrillar ECM components are clearly discerned. It is noticed that ECM does not distribute symmetrically and uniformly. At the tip (marked with the arrow) of the cell cluster, the ECM is sparse, suggesting the cancer cells will metastasize in this direction.

Figure 13C:
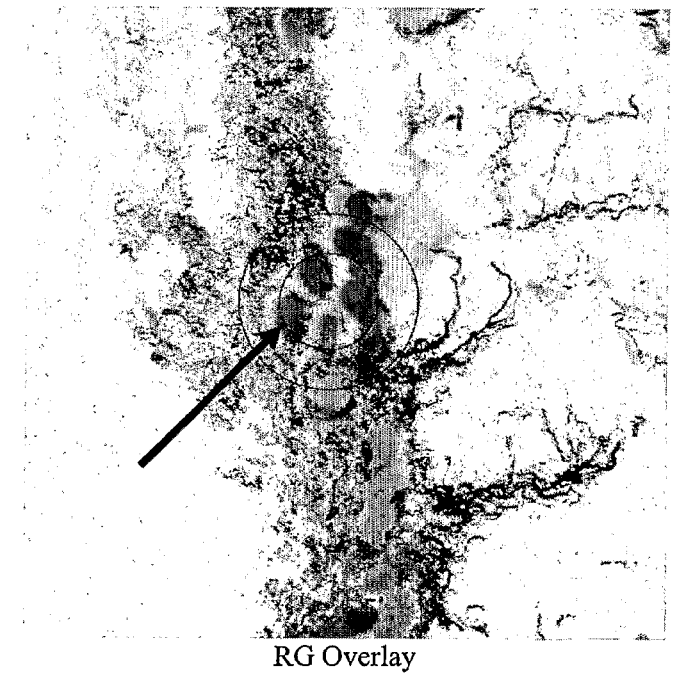
Figure 14:
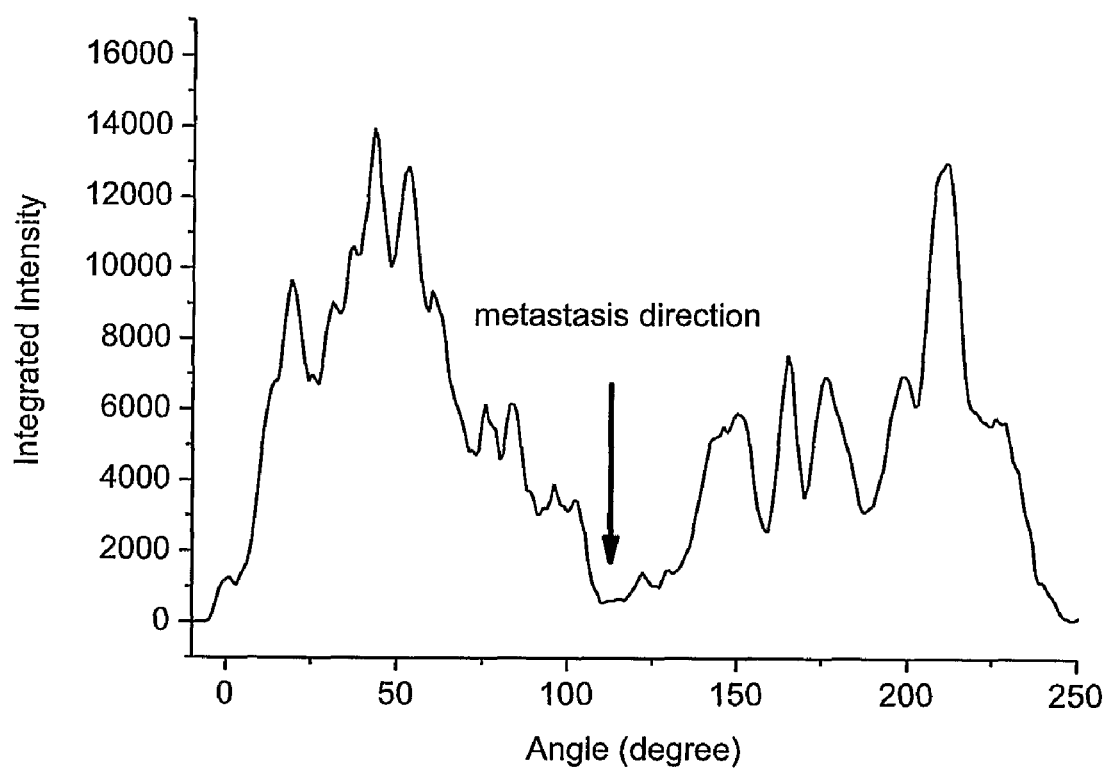
FIG. 14 is a graph of the angular distribution of ECM around the cancer cluster of FIG. 13C.

To obtain quantitative information, the image was first processed with the algorithm described above to remove the noisy background from the image. The centroid of the cancer cells was then chosen. Next, the ECM amount was calculated for different directions. For a given direction, the ECM signal was integrated over a fan shape. In this example, zero degrees is the vertical direction (up) with reference to FIG. 13C and angle increases counter-clockwise in steps of 1 degree. Only the ECM within the ring (marked in each of FIGS. 13A to 13C) was counted to enhance the contrast. FIG. 14 shows a graph of the angular distribution of ECM. The arrow indicating the metastasis direction between about 110 to 115 degrees where the curve displays a deep valley in the integrated intensity, demonstrating ECM in this direction has been degraded.

Conclusions

Through optimizing the parameters and fine tuning the optics systematically, better spatial resolution and higher sensitivity than traditional histological staining methods are able to be achieved using the methods and apparatus described above and demonstrated in Examples 1 to 4 can be achieved through the combination of SHG and TPEF microscopy. With the optimized system and the quantification algorithm developed above, the liver fibrosis process has been successfully monitored from very a early stage. The system does not require any staining of the sample and is able to convey 3D information dynamically for thick tissue slices, even for whole organs, under physiological conditions. The system is also applicable for quantitative studies of tumor ECM dynamics.

It will be appreciated that the methods and/or apparatus and/or systems described and/or illustrated above at least substantially provide an optical imaging apparatus and method for medical analysis of liver tissue and specifically for quantitative characterization of collagen in intact livers tissue structure using nonlinear optical imaging techniques.

The methods and apparatus described herein, and/or shown in the drawings, are presented by way of example only and are not limiting as to the scope of the invention. Unless otherwise specifically stated, individual aspects and components of the methods and apparatus may be modified, or may have been substituted therefore known equivalents, or as yet unknown substitutes such as may be developed in the future or such as may be found to be acceptable substitutes in the future. The methods and apparatus described herein may also be modified for a variety of applications while remaining within the scope and spirit of the claimed invention, since the range of potential applications is great, and since it is intended that the present methods and apparatus be adaptable to many such variations.

What is claimed is:

1. A microscope assembly for optical imaging of biological tissue, the assembly comprising:
   an optical excitation source for irradiating a scan area of a biological tissue sample and generating optical emissions to be emitted from the sample, wherein the sample comprises first and second faces and wherein in use the sample is disposed such that the first face faces away from the excitation source and the second face faces the excitation source;
   a two dimensional scanning element for scanning the light from the excitation source over the scan area of the sample;
   a focussing element having a numerical aperture $NA_1$ disposed to focus light from the excitation source onto the sample;
   a first optical condenser disposed to collect collected light from the first face of the sample, the collected light comprising transmitted light from the excitation source and a first optical emission generated in the sample in response to light from the excitation source, the first optical condenser having a numerical aperture $NA_2$ than the numerical aperture of the optical objective $NA_1$;
   a first optical band-pass filter disposed to block the transmitted light from the excitation source;
   an aperture with an aperture size corresponding to the irradiated area of the sample, the aperture being located for background suppression with respect to the first optical emission at the conjugate image position of the sample generated by the first condenser; and
   a first optical detector disposed to collect collected light from the first face of the sample for detecting the first optical emission from the scan area of the sample;
   wherein the numerical aperture of the first optical condenser is in the range of about 0.5 to about 0.8.

2. A microscope as claimed in claim 1 wherein the first optical emission is a second harmonic signal generated in the sample in response to light from the excitation source.

3. A microscope assembly for optical imaging of biological tissue, the assembly comprising:
   an optical excitation source for irradiating a scan area of a biological tissue sample and generating optical emissions to be emitted from the sample, wherein the sample comprises first and second faces and wherein in use the sample is disposed such that the first face faces away from the excitation source and the second face faces the excitation source;
   a two dimensional scanning element for scanning the light from the excitation source over the scan area of the sample;
   a focussing element having a numerical aperture $NA_1$ disposed to focus light from the excitation source onto the sample;
   a first optical condenser disposed to collect collected light from the first face of the sample, the collected light comprising transmitted light from the excitation source and a first optical emission generated in the sample in response to light from the excitation source, the first optical condenser having a numerical aperture $NA_2$ larger than the numerical aperture of the optical objective $NA_1$;
   a first optical band-pass filter disposed to block the transmitted light from the excitation source;
   an aperture with an aperture size corresponding to the irradiated area of the sample, the aperture being located for background suppression with respect to the first optical emission at the conjugate image position of the sample generated by the first condenser; and
   a first optical detector disposed to collect collected light from the first face of the sample for detecting the first optical emission from the scan area of the sample;
   wherein said microscope further comprises at least one second optical detector disposed to detect a second optical emission from the second face of the sample; and
   wherein the second optical emission comprises at least a second harmonic signal generated in the sample in response to light from the excitation source.

4. A microscope as claimed in claim 3 further comprising a second optical band-pass filter disposed to block the reflected or scattered light from the excitation source from being detected by the second optical detector.

5. A microscope as claimed in claim 1 wherein the transmission bandwidth of the first optical band-pass filter is in the range of about 1 to 30 nm.

6. A microscope as claimed in claim 5 wherein the transmission bandwidth of the first optical band-pass filter is about 10 nm.

7. A microscope as claimed in claim 1 further comprising a collimating lens for collimating the first optical emission from the sample, the collimating lens located intermediate the aperture and the first detector.

8. A microscope as claimed in claim 7 further comprising a second optical condenser disposed to collect the collimated light and direct it to the first detector.

9. A microscope as claimed in claim 1 wherein the first optical emission is a second harmonic optical emission generated in the sample in response to light from the excitation source.

10. A microscope assembly for optical imaging of biological tissue, the assembly comprising:
    an optical excitation source for irradiating a scan area of a biological tissue sample and generating optical emissions to be emitted from the sample, wherein the sample comprises first and second faces and wherein in use the sample is disposed such that the first face faces away from the excitation source and the second face faces the excitation source;
    a two dimensional scanning element for scanning the light from the excitation source over the scan area of the sample;
    a focussing element having a numerical aperture $NA_1$ disposed to focus light from the excitation source onto the sample;
    a first optical condenser disposed to collect collected light from the first face of the sample, the collected light comprising transmitted light from the excitation source and a first optical emission generated in the sample in response to light from the excitation source, the first optical condenser having a numerical aperture $NA_2$ larger than the numerical aperture of the optical objective $NA_1$;
    a first optical band-pass filter disposed to block the transmitted light from the excitation source;
    an aperture with an aperture size corresponding to the irradiated area of the sample, the aperture being located for background suppression with respect to the first optical emission at the conjugate image position of the sample generated by the first condenser; and
    a first optical detector disposed to collect collected light from the first face of the sample for detecting the first optical emission from the scan area of the sample;
    wherein said microscope further comprises:
    an optical spectrometer for selectively detecting the first optical emission from the sample; and
    a repositionable mirror for selectively directing the first optical emission from the sample either to the spectrometer or to the first detector.

11. A microscope as claimed in claim 3 comprising:
    at least two second optical detectors disposed to collect collected light from the second face of the sample for detection of the second optical emission from the second face of the sample at two different wavelengths, each second detector having a respective second optical band-pass filter for selecting a particular optical wavelength band for detection; and
    at least one optical beam splitter for directing a portion of the second optical emission to each of the at least two second detectors.

12. A microscope as claimed in claim 11 wherein the second optical emission from the sample comprises multi-photon excited fluorescence signal of at least two different wavelengths and the at least two second optical detectors are configured to detect the multi-photon excited fluorescence signal at each wavelength.

13. A microscope as claimed in claim 11 wherein the second optical emission from the sample is a multi-photon excited fluorescence signal generated in the sample in response to light from the excitation source.

14. A microscope as claimed in claim 13 wherein the multi-photon excited fluorescence signal is a two-photon excited fluorescence signal.

15. A microscope as claimed in claim 11 wherein the second optical emission from the sample comprises both a multi-photon excited fluorescence signal and a second harmonic generated signal generated in the sample in response to light from the excitation source.

16. A microscope assembly for optical imaging of biological tissue, the assembly comprising:
    an optical excitation source for irradiating a scan area of a biological tissue sample and generating optical emissions to be emitted from the sample, wherein the sample comprises first and second faces and wherein in use the sample is disposed such that the first face faces away from the excitation source and the second face faces the excitation source;
    a two dimensional scanning element for scanning the light from the excitation source over the scan area of the sample;
    a focussing element having a numerical aperture $NA_1$ disposed to focus light from the excitation source onto the sample;
    a first optical condenser disposed to collect collected light from the first face of the sample, the collected light comprising transmitted light from the excitation source and a first optical emission generated in the sample in response to light from the excitation source, the first optical condenser having a numerical aperture $NA_2$ larger than the numerical aperture of the optical objective $NA_1$;
    a first optical band-pass filter disposed to block the transmitted light from the excitation source;
    an aperture with an aperture size corresponding to the irradiated area of the sample, the aperture being located for background suppression with respect to the first optical emission at the conjugate image position of the sample generated by the first condenser;
    a first optical detector disposed to collect collected light from the first face of the sample for detecting the first optical emission from the scan area of the sample;
    at least two second optical detectors disposed to collect collected light from the second face of the sample for detection of the second optical emission from the second face of the sample at two different wavelengths, each second detector having a respective second optical band-pass filter for selecting a particular optical wavelength band for detection; and
    at least one optical beam splitter for directing a portion of the second optical emission to each of the at least two second detectors;
    wherein the second optical emission from the sample comprises both a multi-photon excited fluorescence signal and a second harmonic generated signal generated in the sample in response to light from the excitation source, and wherein one of the two second detectors is configured for detection of the multi-photon excited fluorescence signal and the other second detector is configured for detection of the second harmonic generated signal.

17. A microscope as claimed in claim 1 wherein the optical excitation source is a pulsed laser source.

18. A microscope as claimed in claim 1 wherein the wavelength of the optical excitation source is in the range of about 880 to 900 nm.

19. A microscope assembly for optical imaging of biological tissue, the assembly comprising:
an optical excitation source for irradiating a scan area of a biological tissue sample and generating optical emissions to be emitted from the sample, wherein the sample comprises first and second faces and wherein in use the sample is disposed such that the first face faces away from the excitation source and the second face faces the excitation source;
a two dimensional scanning element for scanning the light from the excitation source over the scan area of the sample;
a focussing element having a numerical aperture $NA_1$ disposed to focus light from the excitation source onto the sample;
a first optical condenser disposed to collect collected light from the first face of the sample, the collected light comprising transmitted light from the excitation source and a first optical emission generated in the sample in response to light from the excitation source, the first optical condenser having a numerical aperture $NA_2$ larger than the numerical aperture of the optical objective $NA_1$;
a first optical band-pass filter disposed to block the transmitted light from the excitation source;
an aperture with an aperture size corresponding to the irradiated area of the sample, the aperture being located for background suppression with respect to the first optical emission at the conjugate image position of the sample generated by the first condenser; and
a first optical detector disposed to collect collected light from the first face of the sample for detecting the first optical emission from the scan area of the sample;
wherein the optical power from the optical excitation source incident on the sample is in the range of about 50 mW to 150 mW.

20. A microscope as claimed in claim 19 wherein the optical power from the optical excitation source incident on the sample is about 80 mW.

21. A microscope as claimed in claim 1 wherein the biological tissue has a high optical scattering coefficient.

22. A microscope as claimed in claim 1 wherein the biological tissue is liver tissue.

23. A method of obtaining an image of a biological tissue sample comprising first and second faces, the method comprising the steps of:
illuminating the biological tissue sample with excitation light from an optical excitation source, the light being scanned over a scan area of the sample, the first face facing away from the excitation source and the second face facing the excitation source, the light being focussed on the sample with focussing element on the second side of the sample, the focussing element having a numerical aperture $NA_1$;
collecting light from the first face of the sample with a first optical condenser, the collected light comprising transmitted light from the excitation source and a first optical emission generated in the sample in response to the excitation light, the first optical condenser having a numerical aperture $NA_2$ larger than the $NA_1$ of the focussing element;
blocking the transmitted light from the excitation source using a first optical band-pass filter;
passing the first optical emission through an aperture with an aperture size corresponding to the irradiated area of the sample, the aperture being located for background suppression with respect to the first optical emission at the conjugate image position of the sample generated by the first condenser; and
detecting the first optical emission from the scan area of the sample using a first optical detector,
wherein the numerical aperture of the first optical condenser is in the range of about 0.5 to about 0.8.

24. A method of obtaining an image of a biological tissue sample comprising the steps of:
using the microscope of claim 1, detecting a first optical emission from the sample over a scan area of the sample irradiated by the optical excitation source to generate at least one first image of the first optical emission;
applying a threshold segmentation method to the first image to generate a second image, the second image being a segmented image of the first image;
using the second image as a mask image, multiplying each pixel in the first image with the corresponding pixel of the second image to generate a third image, wherein in the third image the background noise signal in the first image is removed.

25. A method as claimed in claim 24 wherein a total area characterised by Second Harmonic Generation (SHG) emission and a total intensity of Second Harmonic Generation (SHG) emission in the third image are normalised for comparison with other images obtained from different biological tissue samples.

26. A method as claimed in claim 23 wherein the first optical emission is Second Harmonic Generation (SHG) emission generated in the sample in response to light from the excitation source.

27. A method as claimed in claim 23 wherein the biological tissue has a high optical scattering coefficient.

28. A method as claimed in claim 23 wherein the biological tissue is liver tissue.

29. A method of determining the severity of fibrosis in a biological tissue sample comprising the steps of:
obtaining an image of a biological tissue sample using the method as claimed in claim 24;
determining a normalised intensity of Second Harmonic Generation (SHG) emission generated in the sample in the image; and
relating the normalised intensity of the Second Harmonic Generation (SHG) emission to the amount of collagen in the biological tissue, wherein the amount of collagen present in the sample is related to the severity of fibrosis of the biological tissue sample.

30. A method as claimed in claim 29 wherein the biological tissue has a high optical scattering coefficient.

31. A method as claimed in claim 29 wherein the biological tissue is liver tissue.

32. A method of obtaining an image of a thick biological tissue sample comprising first and second faces, the method comprising the steps of:
irradiating the biological tissue sample with excitation light from an optical excitation source, the light being scanned over a scan area of the sample, the first face facing away from the excitation source and the second face facing the excitation source;
focussing light from the excitation source on to the sample using a focussing element having a numerical aperture $NA_1$;
collecting light from the first face of the sample with a first optical condenser, the first face collected light comprising transmitted light from the excitation source and a first optical emission generated by the sample, the first optical condenser having a numerical aperture $NA_2$ larger than the $NA_1$ of the focussing element;

passing the first optical emission through an aperture with an aperture size corresponding to the irradiated area of the sample, the aperture being located for background suppression with respect to the first optical emission at the conjugate image position of the sample generated by the first condenser;

collecting light from the second face of the sample with the focussing element, the second face collected light comprising a second optical emission from the sample;

detecting the first optical emission from the first face of the sample using a first optical detector; and detecting the second optical emission from the second face of the sample using a second optical detector; and by scanning the excitation source over the scan area, forming first and second images comprising of the biological tissue sample, the first image comprising the first optical emission and the second image comprising the second optical emission generated by the sample;

wherein the first face collected light and the second face collected light each comprise a second harmonic generated signal generated in the sample in response to light from the excitation source.

33. A method as claimed in claim 32 wherein the second face collected light comprises both a multi-photon excited fluorescence signal and a second harmonic generated signal generated in the sample in response to light from the excitation source.

34. A method as claimed in claim 33 further comprising separating the second harmonic generated signal and the multi-photon excited fluorescence signal in the first face collected light and detecting the second harmonic generated signal with the second detector and detecting the multi-photon excited fluorescence signal with a third optical detector.

35. A method of obtaining a three dimensional image of a biological tissue sample comprising the steps of:

repeating the method of claim 32 for a plurality of iterations, wherein, for each iteration the light from the excitation source is focused at a different depth in the biological tissue sample, thereby to obtain a corresponding plurality of two-dimensional images of the biological tissue sample, each image corresponding to the optical emission generated in the sample in response to the excitation light at the corresponding focus depth; and combining the plurality of two-dimensional images into a three-dimensional image of the sample.

36. A method of obtaining a three dimensional image of a biological tissue sample comprising the steps of:

repeating the method of claim 32 for a plurality of iterations, wherein, for each iteration the light from the excitation source is focused at a different depth in the biological tissue sample, thereby to obtain a corresponding plurality of two-dimensional images of the biological tissue sample, each image corresponding to the optical emission generated in the sample in response to the excitation light at the corresponding focus depth; and for each two dimensional image generating a corresponding plurality of segmented images;

masking the plurality of two-dimensional images with the corresponding segmented image to remove the background noise in the two-dimensional image, thereby generating a corresponding plurality of noise-corrected images;

combining the plurality of noise-corrected images into a noise corrected three-dimensional image of the sample.

37. A method as claimed claim 35 further comprising prior to the combining step, normalising either or both the intensity or the area of each of the plurality of images.

38. A microscope as claimed in claim 3 wherein the first optical emission is a second harmonic signal generated in the sample in response to light from the excitation source.

39. A microscope as claimed in claim 3 wherein the transmission bandwidth of the first optical band-pass filter is in the range of about 1 to 30 nm.

40. A microscope as claimed in claim 39 wherein the transmission bandwidth of the first optical band-pass filter is about 10 nm.

41. A microscope as claimed in claim 3 further comprising a collimating lens for collimating the first optical emission from the sample, the collimating lens located intermediate the aperture and the first detector.

42. A microscope as claimed in claim 41 further comprising a second optical condenser disposed to collect the collimated light and direct it to the first detector.

43. A microscope as claimed in claim 3 wherein the first optical emission is a second harmonic optical emission generated in the sample in response to light from the excitation source.

44. A microscope as claimed in claim 3 wherein the optical excitation source is a pulsed laser source.

45. A microscope as claimed in claim 3 wherein the wavelength of the optical excitation source is in the range of about 880 to 900 nm.

46. A microscope as claimed in claim 3 wherein the biological tissue has a high optical scattering coefficient.

47. A microscope as claimed in claim 3 wherein the biological tissue is liver tissue.

48. A method of obtaining an image of a biological tissue sample comprising the steps of:

using the microscope of claim 3, detecting a first optical emission from the sample over a scan area of the sample irradiated by the optical excitation source to generate at least one first image of the first optical emission;

applying a threshold segmentation method to the first image to generate a second image, the second image being a segmented image of the first image;

using the second image as a mask image, multiplying each pixel in the first image with the corresponding pixel of the second image to generate a third image, wherein in the third image the background noise signal in the first image is removed.

49. A method as claimed in claim 48 wherein a total area characterised by Second Harmonic Generation (SHG) emission and a total intensity of Second Harmonic Generation (SHG) emission in the third image are normalised for comparison with other images obtained from different biological tissue samples.

50. A method of determining the severity of fibrosis in a biological tissue sample comprising the steps of:

obtaining an image of a biological tissue sample using the method as claimed in claim 48;

determining a normalised intensity of Second Harmonic Generation (SHG) emission generated in the sample in the image; and relating the normalised intensity of the Second Harmonic Generation (SHG) emission to the amount of collagen in the biological tissue, wherein the amount of collagen present in the sample is related to the severity of fibrosis of the biological tissue sample.

51. A method as claimed in claim 50 wherein the biological tissue has a high optical scattering coefficient.

52. A method as claimed in claim 50 wherein the biological tissue is liver tissue.

* * * * *